US010864253B2

(12) United States Patent
Brines et al.

(10) Patent No.: US 10,864,253 B2
(45) Date of Patent: Dec. 15, 2020

(54) TISSUE PROTECTIVE PEPTIDES FOR PREVENTING AND TREATING DISEASES AND DISORDERS ASSOCIATED WITH TISSUE DAMAGE

(71) Applicant: Araim Pharmaceuticals, Inc., Tarrytown, NY (US)

(72) Inventors: Michael Brines, Woodbridge, CT (US); Anthony Cerami, La Jolla, CA (US)

(73) Assignee: Araim Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/096,247

(22) PCT Filed: Apr. 28, 2017

(86) PCT No.: PCT/US2017/030100
§ 371 (c)(1),
(2) Date: Oct. 24, 2018

(87) PCT Pub. No.: WO2017/189988
PCT Pub. Date: Nov. 2, 2017

(65) Prior Publication Data
US 2019/0134156 A1 May 9, 2019

Related U.S. Application Data

(60) Provisional application No. 62/329,743, filed on Apr. 29, 2016.

(51) Int. Cl.
| *A61K 38/00* | (2006.01) |
| *A61K 38/04* | (2006.01) |
| *A61K 38/18* | (2006.01) |
| *C07K 14/47* | (2006.01) |
| *A61P 31/12* | (2006.01) |
| *A61P 29/00* | (2006.01) |
| *A61P 35/00* | (2006.01) |
| *C12N 15/85* | (2006.01) |
| *C07K 5/103* | (2006.01) |

(52) U.S. Cl.
CPC .............. *A61K 38/18* (2013.01); *A61K 38/04* (2013.01); *A61P 29/00* (2018.01); *A61P 31/12* (2018.01); *A61P 35/00* (2018.01); *C07K 5/1008* (2013.01); *C07K 14/47* (2013.01); *C12N 15/85* (2013.01); *A61K 38/00* (2013.01)

(58) Field of Classification Search
CPC ........ A61K 38/00; A61K 38/04; A61K 38/18; A61P 29/00; A61P 31/12; A61P 35/00; C07K 14/47; C07K 5/1008; C12N 15/85
USPC ........... 514/1.1, 21.3, 21.4, 21.5, 21.6, 21.7, 514/21.8, 21.9; 530/300, 324, 325, 326, 530/327, 328, 329, 330
See application file for complete search history.

(56) References Cited

U.S. PATENT DOCUMENTS

| 4,055,635 | A | 10/1977 | Green et al. |
| 4,088,538 | A | 5/1978 | Schneider |
| 4,414,147 | A | 11/1983 | Klibanov et al. |
| 4,496,689 | A | 1/1985 | Mitra |
| 5,051,448 | A | 9/1991 | Shashoua |
| 5,192,746 | A | 3/1993 | Lobl et al. |
| 5,559,103 | A | 9/1996 | Gaeta et al. |
| 5,576,423 | A | 11/1996 | Aversa et al. |
| 7,767,643 | B2 | 8/2010 | Brines et al. |
| 8,853,358 | B2 | 10/2014 | Cerami et al. |
| 9,046,530 | B2* | 6/2015 | Zhong ................. G01N 33/6893 |
| 2003/0072737 | A1 | 4/2003 | Brines et al. |
| 2013/0143757 | A1* | 6/2013 | Zhong ................. G01N 33/6893 506/9 |
| 2014/0127134 | A1 | 5/2014 | Yang et al. |
| 2015/0031858 | A1 | 1/2015 | Powell et al. |
| 2015/0126714 | A1* | 5/2015 | Chin ..................... C07K 16/24 530/387.9 |

FOREIGN PATENT DOCUMENTS

| CA | 2940078 | 9/2015 |
| EP | 2703487 | 3/2017 |
| WO | WO 1987/000056 | 1/1987 |
| WO | WO 1994/005332 | 3/1994 |
| WO | WO 2002/053580 | 7/2002 |
| WO | WO 2004/022577 | 9/2004 |
| WO | WO 2005/025606 | 3/2005 |
| WO | WO 2005/032467 | 4/2005 |
| WO | WO 2006/083301 | 8/2006 |
| WO | WO 2007/019545 | 2/2007 |
| WO | WO 2009/094172 | 7/2009 |
| WO | WO 2015/009820 | 1/2015 |
| WO | WO 2015/131858 | 9/2015 |

OTHER PUBLICATIONS

UniProt Q7ZXK5, pp. 1-5. (Year: 2003).*
UniProt H0YDT3, pp. 1-5. (Year: 2012).*
Brines et al., "Nonerythropoietic, tissue-protective peptides derived from the tertiary structure of erythropoietin," *Proc. Natl. Acad. Sci. USA*, 105(31):10925-10930 (2008).
Grace et al.., "NMR structure and peptide hormone binding site of the first extracellular domain of a type B1 G protein-coupled receptor," *Proc. Natl. Acad. Sci. USA*, 101:12836-12841 (2004).
International Patent Application No. PCT/US2017/030100, International Search Report dated Oct. 2, 2017.
International Patent Application No. PCT/US2017/030100, International Preliminary Report on Patentability dated Nov. 8, 2018.

(Continued)

*Primary Examiner* — Julie Ha
(74) *Attorney, Agent, or Firm* — Jones Day

(57) ABSTRACT

Provided herein are peptides and peptide analogs that have tissue protective activities. The peptides and peptide analogs are useful in preventing and treating a variety of diseases and disorders associated with tissue damage.

Figure 1:
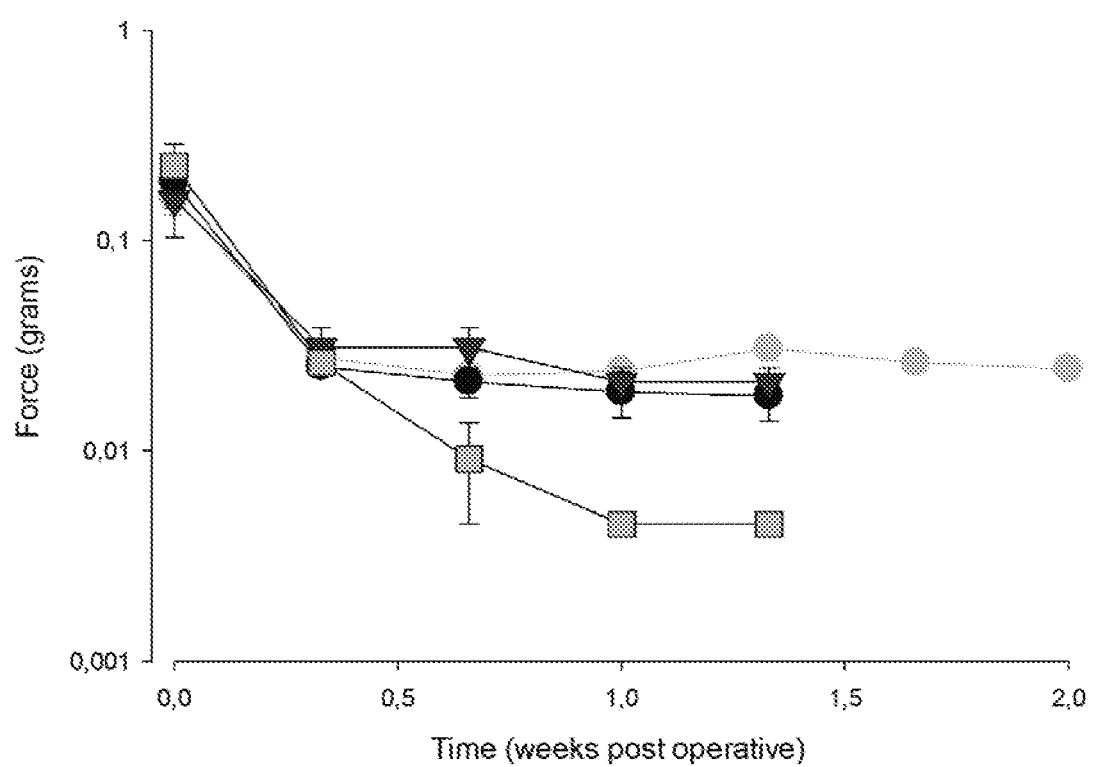

5 Claims, 3 Drawing Sheets
Specification includes a Sequence Listing.

(56) References Cited

OTHER PUBLICATIONS

International Patent Application No. PCT/US2017/030100, Written Opinion dated Oct. 2, 2017.
Kinoshita et al., "HMG-X, a Xenopus gene encoding an HMG1 homolog, is abundantly expressed in the developing nervous system," *FEBS Letters*, 352(2):191-196 (1994).

* cited by examiner

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: Tissue protective peptide

<400> SEQUENCE: 1

Gly Asp Lys Ala Arg Tyr Glu Arg Glu Met
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Tissue protective peptide

<400> SEQUENCE: 2

Gly Asp Lys Ala Arg Tyr Glu Arg Glu Ala
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Tissue protective peptide

<400> SEQUENCE: 3

Gly Asp Lys Ala
1

<210> SEQ ID NO 4
<211> LENGTH: 12
<212> TYPE: PRT
<213> ORGANISM: Artificial Sequence
<220> FEATURE:
<223> OTHER INFORMATION: Amphipathic peptide: calcitonin - Peptide A

<400> SEQUENCE: 4

Ala Leu Ser Ile Leu Val Leu Leu Gln Ala Gly Ser
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: Amphipathic peptide: Peptide B -
      corticotropin releasing hormone

<400> SEQUENCE: 5

Val Ala Leu Leu Pro Cys Pro Pro Cys Arg Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Amphipathic peptide: Peptide C
      - beta endorphin

<400> SEQUENCE: 6

Asn Ala Ile Ile Lys Asn Ala Tyr Lys Lys Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Amphipathic peptide: Peptide D - glucagon

<400> SEQUENCE: 7

Gly Ser Trp Gln Arg Ser Leu Gln Asp Thr Glu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Amphipathic peptide: Peptide E - secretin

<400> SEQUENCE: 8

Gly Gly Ser Ala Ala Arg Pro Ala Pro Pro
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Amphipathic peptide: Peptide F -
      vasointestinal peptide

<400> SEQUENCE: 9

Asn Ala Leu Ala Glu Asn Asp Thr Pro Tyr Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Amphipathic peptide: Peptide G -
      neuropeptide Y

<400> SEQUENCE: 10
```

-continued

```
Gly Ala Leu Ala Glu Ala Tyr Pro Ser Lys Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Amphipathic peptide: Peptide H -
      gonadotropin releasing hormone

<400> SEQUENCE: 11

Gly Cys Ser Ser Gln His Trp Ser Tyr Gly Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Amphipathic peptide: Peptide I -
      parathyroid hormone

<400> SEQUENCE: 12

Val Met Ile Val Met Leu Ala Ile Cys Phe Leu
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Amphipathic peptide: Peptide J -
      pancreatic polypeptide

<400> SEQUENCE: 13

Leu Arg Arg Tyr Ile Asn Met Leu Thr Arg Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Amphipathic peptide: Peptide K -
      calcitonin gene related peptide

<400> SEQUENCE: 14

Leu Ala Leu Ser Ile Leu Val Leu Tyr Gln Ala
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Chimeric peptide of SEQ ID NO: 3 and 14

<400> SEQUENCE: 15

Gly Asp Lys Ala Leu Arg Arg Tyr Ile Asn Met Leu Thr Arg Pro
1               5                   10                  15

<210> SEQ ID NO 16
<211> LENGTH: 16
<212> TYPE: PRT
<213> ORGANISM: Artificial Sequence
<220> FEATURE:
```

```
<223> OTHER INFORMATION: Chimeric peptide of SEQ ID NO: 3 and 14 with TR
      replacement

<400> SEQUENCE: 16

Gly Asp Lys Ala Leu Arg Arg Tyr Ile Asn Met Leu Thr Arg Thr Arg
1               5                   10                  15
```

TISSUE PROTECTIVE PEPTIDES FOR PREVENTING AND TREATING DISEASES AND DISORDERS ASSOCIATED WITH TISSUE DAMAGE

CROSS REFERENCE TO RELATED APPLICATIONS

This application is a U.S. National Stage Application under 35 U.S.C. § 371 of International Patent Application No. PCT/US2017/030100, filed Apr. 28, 2017, which claims the benefit of priority of U.S. Provisional Application Ser. No. 62/329,743, filed Apr. 29, 2016, the entire contents of which are each incorporated herein by reference.

REFERENCE TO SEQUENCE LISTING SUBMITTED ELECTRONICALLY

This application incorporates by reference a sequence listing submitted with this application as text file entitled "12110-025-999_Sequence_Listing.TXT" created on Oct. 18, 2018 and having a size of 4,197 bytes

1. INTRODUCTION

Provided herein are tissue protective peptides and peptide analogs for preventing or treating a disease or disorder associated with tissue damage and/or damage associated with an effect, or a symptom of the disease or disorder, including, but not limited to, cancer, inflammation, and exposure to a toxic agent. Further provided are methods and uses of these peptides to modulate a subject's response and/or a symptom resulting from a disease or disorder associated with tissue damage for the purposes of treating, preventing or ameliorating the disease or disorder.

Additionally, provided herein are pharmaceutical compositions comprising a peptide and a pharmaceutically acceptable carrier, excipient or diluent for the treatment of a disease or disorder associated with tissue damage; or damage associated with an effect, or a symptom of the disease or disorder, including, but not limited to, cancer, inflammation and exposure to a toxic agent, in a subject in need thereof.

2. BACKGROUND

Tissue damage can be caused by a substantive loss of tissue due to, for example, ischemic, traumatic, toxic, or inflammatory injuries in which cells within the tissue are destroyed by apoptosis or necrosis. Tissue damage can occur in a number of acute and chronic diseases and conditions. The degree to which tissue damage occurs is mediated by many factors, including the type of disease or injury, the level of or severity of inflammation or trauma associated with the disease or injury, the location of the tissue damage, and the vascular sufficiency of the tissue.

Accordingly, there is a need for tissue protective treatments that have little or no potentially detrimental effects and can be made readily available to the public.

3. SUMMARY

Provided herein are isolated peptides and peptide analogs that have tissue protective activity in a responsive cell, tissue, or organ. In certain embodiments, provided herein are tissue protective peptides and peptide analogs that share a consensus sequence of GDKA (SEQ ID NO: 3). In certain embodiments, the peptide consists of the amino acid sequence GDKARYEREM (SEQ ID NO:1). In another embodiment, the peptide comprises the amino acid sequence GDKARYEREM (SEQ ID NO:1). In another embodiment, the peptide consists of the amino acid sequence GDKARYEREA (SEQ ID NO:2). In another embodiment, the peptide comprises the amino acid sequence GDKARYEREA (SEQ ID NO:2). In another embodiment, the peptide consists of the amino acid sequence GDKA (SEQ ID NO:3). In another embodiment, the peptide comprises the amino acid sequence GDKA (SEQ ID NO:3).

In certain embodiments, an isolated peptide or peptide analog provided herein comprises 4 to about 30 amino acids in length, featuring an amino acid sequence of a peptide provided herein. In certain embodiments, an isolated peptide provided herein has from 10 to 30 amino acids in length and includes the amino acid sequence of GDKARYEREM (SEQ ID NO:1) or GDKARYEREA (SEQ ID NO:2). In certain embodiments, an isolated peptide provided has from 4 to 30 amino acids in length and includes the amino acid sequence of GDKA (SEQ ID NO:3). Such isolated peptides also have tissue protective activity in a responsive cell, tissue, or organ as described herein.

In certain embodiments, provided herein are isolated peptides and peptide analogs that have at least one tissue protective activity. Exemplary tissue protective activities include, but are not limited to, protecting, maintaining, enhancing, and restoring the function or viability of a responsive mammalian cell, tissue, or organ. Accordingly, in one embodiment, provided herein is the use of isolated peptides and peptide analogs provided herein for the preparation of pharmaceutical compositions for protecting, maintaining, enhancing, or restoring the function or viability of responsive mammalian cells and their associated cells, tissues, and organs. In related embodiments, the pharmaceutical compositions are for administration to a subject in need thereof.

Provided herein are pharmaceutical compositions comprising such tissue protective peptides and peptide analogs and a pharmaceutically acceptable carrier excipient or diluent, as well as methods for preparing such compositions and their use to treat diseases and disorders associated with tissue damage. In other aspects, provided herein are methods of using an isolated peptide or peptide analog described herein for the preparation of a pharmaceutical composition for the protection against or prevention of a responsive tissue injury, for the restoration of, or for the rejuvenation of responsive tissue or responsive tissue function in a subject in need thereof. In one particular aspect, the responsive mammalian cells and their associated cells, tissues, or organs are distal to the vasculature by virtue of a tight endothelial cell barrier. In another particular aspect, the cells, tissues, organs or other bodily parts are isolated from a mammalian body, such as those intended for transplant. In one aspect, the cells, tissues, or organs are excitable. In certain aspects, the excitable tissue is central nervous system tissue, peripheral nervous system tissue, cardiac tissue or retinal tissue. In another aspect, the responsive cell or its associated cells, tissues, or organs are not excitable cells, tissues, or organs, nor do they predominantly comprise excitable cells or tissues.

In another embodiment, provided herein are methods of preventing, treating, ameliorating or managing inflammation, cancer or neoplastic disorders, or exposure to a toxic agent in a patient in need thereof by administering an effective amount of a peptide.

In certain embodiments, provided herein are methods of modulating the activity of a mediator of cancer, the body's response to toxic agents, and inflammation. In particular, the methods relate to modulating the activity of an inflammatory mediator. In certain embodiments, the peptides provided herein are capable of modulating the effects of one or more inflammatory mediators.

In another embodiment, provided herein are methods of arresting the growth of a cell comprising contacting a cell in need of growth arrestent with an effective amount of a peptide.

In another embodiment, provided herein are methods of causing the death of a cancer or neoplastic cell comprising contacting a cancer or neoplastic cell with an effective amount of a peptide.

In another embodiment, provided herein are methods of inhibiting blood vessel generation to the cancerous or neoplastic cells or reducing the production of molecules causing mitosis or angiogenesis.

In another embodiment, provided herein are methods for treating or preventing the side-effects associated with chemotherapy or radiation therapy, comprising administering to a patient in need of such treatment or prevention an effective amount of a peptide. Side-effects associated with chemotherapy or radiation therapy include cachexia, low blood count, nausea, diarrhea, oral lesions, and alopecia.

In another embodiment, provided herein are methods for treating or preventing cancer or neoplastic disease in a patient comprising contacting a cancer or neoplastic cell with an effective amount of a peptide.

In another embodiment, provided herein are methods of treating or preventing cancer or neoplastic disease in a patient comprising administering to a patient in need of such treatment or prevention an effective amount of a peptide.

In certain embodiments, provided herein are uses of the peptide for the preparation of a pharmaceutical composition for the prevention, treatment, amelioration, or management of a disease or disorder described herein, including, but not limited to cancer or neoplastic disorder in a subject in need thereof.

In another embodiment, provided herein are methods of treating or preventing the symptoms associated with inflammation or an inflammatory condition. In a further embodiment, provided herein are methods of treating or preventing inflammation or an inflammatory condition in a patient in need thereof. Amongst the inflammatory conditions treatable by the method are allergies and allergic diseases, rheumatic diseases, and sports related injuries.

In another embodiment, provided herein are methods of treating, preventing, ameliorating or managing the effects of exposure to a toxic agent in a person in need of treatment. Amongst the toxic agents considered are biological, chemical and radioactive agents.

In another embodiment, provided herein are methods of treating, preventing, ameliorating or managing the symptoms or effects of a disease or disorder of the central nervous system or of the peripheral nervous system.

In another embodiment, provided herein are methods of treating, preventing, ameliorating or managing the symptoms or effects of trauma and/or inflammation of the peripheral nerves of a subject, such as, but not limited to, that of a sciatic nerve injury, reduction in epidermal nerve fibers, neuropathy, pain, neuropathic pain, neuralgia, post-herpetic neuralgia, sarcoid small fiber neuropathy, back pain, diabetic neuropathy or carpal tunnel syndrome. In one embodiment, provided herein is a method of treating, preventing, ameliorating or managing neuropathy or neuropathic pain.

In another embodiment, provided herein are methods of treating, preventing, ameliorating or managing the symptoms of an endocrine or metabolic abnormality in a subject, such as diabetes mellitus type I or diabetes mellitus type II or prediabetes.

In another embodiment, provided herein are methods of treating, preventing, ameliorating or managing the symptoms of aging.

In certain embodiments, provided herein are pharmaceutical compositions comprising the aforementioned isolated peptides for administration to a subject in need thereof. In specific aspects, in accordance with this embodiment, the pharmaceutical composition provided herein further comprises a pharmaceutically acceptable carrier. Such pharmaceutical compositions may be formulated for oral, intranasal, ocular, intranasal, inhalational, transdermal, rectal, sublingual, vaginal, or parenteral administration, or in the form of a perfusate solution for maintaining the viability of cells, tissues, or organs ex vivo. In related embodiments, the subject is a mammalian animal, e.g. a human.

These and other features, aspects, and advantages of the present disclosure will become better understood with reference to the following description and appended claims.

4. ABBREVIATIONS AND TERMINOLOGY 4.1 Abbreviations

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

4.2 Terminology

Unless defined otherwise, all technical and scientific terms used herein have the meaning commonly understood by a person skilled in the art to which the provided peptides, methods, compositions and uses belong. As used herein, the following terms have the meanings ascribed to them unless specified otherwise.

(i) As used herein, the terms "about" or "approximately" when used in conjunction with a number refer to any number within 1, 5, 10, 15 or 20% of the referenced number.

(ii) The term "administered in conjunction with" in the context of the methods provided herein means administering a compound prior to, at the same time as, and/or subsequent to the onset of a disease, disorder, or condition.

(iii) The term "allergen" refers to an antigenic substance capable of producing immediate type hypersensitivity (allergy). Common allergens include, but are not limited to bacteria, viruses, animal parasites, insects and insect stings, chemicals (latex), dust, dust mites, molds, animal dander, drugs (such as antibiotics, serums, sulfa drugs, anti-convulsants, insulin preparations, local anesthetics, iodine, and aspirin), foods (such as milk, chocolate, strawberries, eggs, soy, nuts, fish, shellfish, wheat), perfumes, plants, pollens, and smoke.

(iv) The term "allergic disease" refers to a condition or disease caused by or relating to an allergy. Allergic diseases include, but are not limited to, asthma, hypersensitivity lung diseases, rhinitis, rhinosinusitis, atopic eczema, contact dermatitis, allergic conjunctivitis (intermittent and persistent), vernal conjunctivitis (hayfever), atopic keratoconjunctivitis, giant papillary conjunctivitis, urticaria (hives), angioedema, hypersensitivity pneumonitis, eosinophilic bronchitis, vasculitis, hypersensitivity vasculitis, antineutrophil cytoplasmic antibody (ANCA) associated vasculitis, Wegner's granulomatosis, histamine response, Churg Strauss vasculitis, microscopic polyangiitis, temporal arteritis, celiac disease, mastocytosis, and anaphylaxis.

(v) The term "allergy symptom" or "allergic reaction" refers to the body's response to an allergen. The allergic reaction can be localized to one area (skin that came into contact with allergen) or generalized. Allergic reactions may include, but are not limited to, rash, itching, hives, swelling, difficulty breathing, wheezing, angioedema, difficulty swallowing, nasal congestion, runny nose, shortness of breath, nausea, stomach cramps, abdominal pain, vomiting and/or low blood pressure.

(vi) The term "allergy" refers to a state of hypersensitivity induced by exposure to a particular antigen (allergen) resulting in harmful immunological reactions on subsequent exposures.

(vii) The term "amino acid" or any reference to a specific amino acid is meant to include naturally occurring proteogenic amino acids as well as non-naturally occurring amino acids such as amino acid analogs. Those skilled in the art would know that this definition includes, unless otherwise specifically noted, naturally occurring proteogenic (L)-amino acids, their optical (D)-isomers, chemically modified amino acids, including amino acid analogs such as penicillamine (3-mercapto-D-valine), naturally occurring non-proteogenic amino acids such as norleucine and chemically synthesized amino acids that have properties known in the art to be characteristic of an amino acid. Additionally, the term "amino acid equivalent" refers to compounds that depart from the structure of the naturally occurring amino acids, but which have substantially the structure of an amino acid, such that they can be substituted within a peptide, which retains its biological activity despite the substitution. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents. Amino acids may also be classified into the following groups as is commonly known in the art: (1) acidic=Asp, Glu; (2) basic=Lys, Arg, His; (3) nonpolar (hydrophobic)=Cys, Ala, Val, Leu, Ile, Pro, Phe, Met, Trp, Gly, Tyr; and (4) uncharged polar=Asn, Gln, Ser, Thr. Non-polar may be subdivided into: strongly hydrophobic=Ala, Val, Leu, Ile, Met, Phe; and moderately hydrophobic=Gly, Pro, Cys, Tyr, Trp. In alternative fashion, the amino acid repertoire can be grouped as (1) acidic=Asp, Glu; (2) basic=Lys, Arg, His, (3) aliphatic=Gly, Ala, Val, Leu, Ile, Ser, Thr, with Ser and Thr optionally be grouped separately as aliphatic-hydroxyl; (4) aromatic=Phe, Tyr, Trp; (5) amide=Asp, Glu; and (6) sulfur-containing=Cys and Met. (See, for example, Biochemistry, 4th ed., Ed. by L. Stryer, WH Freeman and Co., 1995, which is incorporated by reference herein in its entirety).

(viii) The term "biological agent" as used herein refers to living organisms or the materials derived from them (such as bacteria, viruses, fungi, and toxins) that cause disease in or harm to humans, animals, or plants, or cause deterioration of materials. These biological agents are ubiquitous in nature and may be designed or optimized for use in warfare or terrorism (bioterrorism). These biological agents may consist of prions, viruses, microorganisms (bacteria and fungi), and some unicellular and multicellular eukaryotes (i.e., parasites). In particular, the biological agents (identified by their common name, biologic name and the NATO Standard Reference letter code, where available) may include, but are not limited to, mycotic agents (*Coccidioides mycosis*, OC, *Coccidioides posadasil, Coccidioides immitis*), bacterial agents (anthrax (cutaneous, inhalation, gastrointestinal) (*Bacillus anthracis*, N and TR), plague (bubonic, pneumonic) (*Yersinia pestis*, LE), tularemia (*Francisella tularensis*, UL (schu S4), TT (wet type), ZZ (dry type) and SR and JT (425)), cholera (*Vibrio cholerae*, HO), bovine brucellosis (AB), porcine brucellosis (US and NX), caprine brucellosis (AM and BX), *Brucella abortus, Brucella melitenis, Brucella suis*, bacterial dysentery (shigellosis, campylobacteriosis, *salmonellosis*) (Y), glanders (*Burkholderia mallei*, LA), melioidosis (*Burkholderia pseudomallei*, HI), diphtheria (*Corynebacterium diphtherias*, DK), listeriosis (*Listeria monocytogenes*, TQ)), chlamydial agents (psittacosis "Parrot Fever" (*Chlamydophilia psittici,* SI), rickettsial agents (rocky mountain spotted fever (*Rickettsia rickettsii*, RI and UY), Q fever (*Coxiella burnetti*, OU, MN (wet type), and NT (dry type)), human typhus (*Rickettsia prowazekii*, YE), murine typhus (*Rickettsia typhi*, AV)), viral agents (yellow fever (*Arbovirus flavivirdae*, OJ, UT, and LU), rift valley fever (RVF *Phlebovirus bunyaviridae*, FA), alphaviruses (e.g.: eastern equine encephalitis (ZX), western equine encephalitis, Venezuelan equine encephalitis (NU, TD, and FX)), smallpox (ZL), Japanese B Encephalitis (AN), Cercopithecine herpesvirus 1 (Herpes B virus), Crimean-Congo haemorrhagic fever virus, viral hemorrhagic fever (Filoviridae (ebola and Marburg virus) and Arenaviridae (Lassa and Machupo)), monkey pox virus, Reconstructed 1918 influenza virus, South American Haemorrhagic Fever viruses (Flexal, Guanarito, Junin, Machupo, Sabia), tick borne meningoencephalitis (TEBV) viruses (Central European Tick-borne encephalitis, Far Eastern Tick-borne encephalitis, Kyasanur Forest disease, Omsk Hemorrhagic fever, Russian Spring and Summer virus), Hendra virus, Nipah virus, hantaviruses (Korean hemorrhagic fever), African horse sickness virus, optimized swine fever virus, Akabane virus, avian influenza virus, bluetongue virus, camel pox virus, classical swine fever virus, foot-and-mouth disease virus, goat pox virus, lumpy skin disease virus, malignant catarrhal fever virus (Alcelaphine herpesvirus type 1), Menangle virus, New Castle disease virus, Pestes des petits ruminants virus, rabies virus, rinderpest virus, sheep pox virus, swine vescular disease virus, vesicular somatitis virus), toxins (botulinum toxin (*Clostridium*, X and XR), ricin (*Ricinus communis*, W and WA), Staphylococcal enterotoxin B (UC and PG), Saxitoxin (paralytic shellfish poisoning)(TZ and SS), tetrodotoxin (PP), conotoxins, *Clostridium perfringens* epsilon toxin, tricothecene mycotoxins (T-2 toxins), shigatoxin), and simuants (molasis residium (MR), *Bacillus globigii* (BG, BS, and U), *Serratia marescens* (SM and P), *Aspergillus fumigatus* mutant C-2 (AF), *E. Coli* (EC), *Bacillus thursidius* (BT), *Erwinia her-*

*bicola* (EH), fluorescent particle (FP)), rye ergot, leprosy, rabies, intestinal typhoid, *Clostridium perfringens* (gas gangrene), aflatoxins, *Salmonella typhimurium*, enterotoxins, Argentinian hemorrhagic fever, multi-drug resistant Tuberculosis (MTB), Bolivian hemorrhagic fever, legionella pneumophilia, marine toxins, beriberi, malaria, pellagra, dengue fever, sclerotium rolfoil, neurotrophic encephalitis, *Shigella* (Y), SEB (UC), and mycotoxins, Diaacetoxyscirpenol, *Cowdria ruminantium, Mycoplasma capricolum* M.F38/M. *Mycoides capri, Mycoplasma mycoides mycoides*, abrin. The biological agents may be targeted against humans (e.g. Small pox, Ebola virus, Reconstructed 1918 influenza virus, ricin, etc.), animals such as livestock (e.g. African horse sickness virus, African swine fever virus, foot-and-mouth disease, etc.) or both (Eastern equine encephalitis virus, etc.) Further, even non-lethal biological agents may pose a threat given that they may be re-engineered for greater lethality for use as a biological weapon. Thus even the viruses responsible for the common cold may pose a risk.

(ix) The term "cancer" as used herein refers to any abnormal growth exhibiting malignant properties: the ability (1) to grow and divide without respect to normal limits, (2) to invade and destroy adjacent tissues, and (3) in some instances, spread to other locations in the body. Cancer includes cancers or neoplastic disorders of the central nervous system, peripheral nervous system, gastrointestinal/digestive system, genitourinary system, gynecological, head and neck, hematological/blood, musculoskeletal/soft tissue, respiratory, and breast. Further examples of cancers or neoplastic disorders include, but are not limited to, those of the brain (astrocytoma, gliobastoma, glioma), spinal cord, pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), Lymph node cancer, Lung (Adenocarcinoma, Oat Cell, Non-small Cell, Small Cell, Squamous Cell, Mesothelioma), skin (melanoma, basal cell, squamous cell, Kaposi's Sarcoma), Bone Cancer (Ewings Sarcoma, Osteosarcoma, Chondrosarcoma), head and neck (laryngeal, pharyngeal (nasal cavity & sinus cavity), and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), genitourinary (bladder, kidney, penile, prostate, testicular, and urinary cancers), adrenal (cortical adenoma, cortical carcinoma, pheochromocytoma) and gastrointestinal (appendix, bile duct (extrahepatic bile duct) colon, gallbladder, gastric, intestinal, colon, liver, pancreatic, rectal, and stomach cancers) as well as those listed below: (for a review of such disorders, see Fishman et al., 1985, Medicine, 2d Ed., J.B. Lippincott Co., Philadelphia): Leukemia: acute leukemia, acute lymphocytic leukemia, acute myelocytic leukemia, myeloblastic, promyelocytic, myelomonocytic, monocytic erythroleukemia, chronic leukemia, chronic myelocytic (granulocytic) leukemia, chronic lymphocytic leukemia, Polycythemia vera, Gastric carcinoma, Lymphoma (malignant and non-malignant): Hodgkin's disease, non-Hodgkin's disease, Multiple myeloma, Waldenstrom's macroglobulinemia, Heavy chain disease, solid tumors, Solid tumors sarcomas and carcinomas: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, oral squamous cell carcinoma, hepatocellular carcinoma, basal cell carcinoma, adenocarcinoma, sweat gland carcinoma, sebaceous gland carcinoma, papillary carcinoma, papillary adenocarcinomas: cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, cervix adenocarcinoma, uterine cancer, testicular tumor, lung carcinoma, small cell lung carcinoma, non-small cell lung adenocarcinoma, bladder carcinoma, epithelial carcinoma, glioma, malignant glioma, glioblastoma, multiforme astrocytic gliomas, medulloblastoma, craniopharyngioma, ependymoma, pinealoma, hemangioblastoma, acoustic neuroma, oligodendroglioma, meningioma, melanoma, neuroblastoma, or retinoblastoma.

(x) The term "chemical agent" as used herein refers chemical substances that cause severe death or harm to people or animals. To the extent that the chemical agent has been optimized to be delivered using munitions or a dispersal device, the agent is a chemical weapon. In general, chemical agents used as weapons can be classified by their method of action such as: blood agents, blister agents, nerve agents, pulmonary agents, and incapacitating agents. Each of the chemical agents below is identified by their NATO standard Reference letter code where available.

(xi) "Blood agents" refer to those chemical agents that prevent cells from using oxygen. Chemical agents within this category include, but are not limited to Arsine (adamsite (diphenylaminechloroarsine), Clark I (diphenylchloroarsine), Clark II (diphenylcyanoarsine)) and Cyanide (cyanogen chloride (CK), hydrogen cyanide (AC), etc.) compounds. Arsine compounds cause intravascular hemolysis that leads to renal failure. Cyanide compounds prevent the cells from using oxygen and the cells then resort to anaerobic respiration creating an excess of lactic acid leading to metabolic acidosis. Victims of blood agents may exhibit symptoms including, but not limited to, headaches, dizziness, nausea, vomiting, mucosal irritation, dysponea, impaired consciousness, coma, convulsions, tachy- and brady-dysrhythmias, hypotension, cardiovascular collapse, and acyanosis.

(A) "Nerve agents" refer to those chemical agents that inactivate the enzyme acetylcholinesterase. The resulting buildup of the neurotransmitter acetylcholine in the victim's synapses leads to muscarinic and nicotinic effects. Compounds within this category include, but are not limited to, cyclosarin (cyclohexylmethylphosphofluoridate, GF), sarin (isopropyl methylphosphanofluoridate, GB), thiosarin, soman (pinacolylmethylphosphanofluoridate, GC), tabun (ethyl N, N-dimethylphosphoramidocyanidate, GA), VX (O-ethyl-[s]-[2-diisopropylaminoethyl-methylphosphonothiolate), VR (N,N-diethyl-2-(methyl-(2-methylpropoxy)phosphoryl)sulfanylethanamine), VE (O-ethyl-S-[2-(diethylamino)ethyl]phosphonothioate), VG (0,0-diethyl-S-[2-(diethylamino)ethyl]phosphorothioate), VM (O-ethyl-S-[2-(diethylamino)ethyl]methylphosphonothioate), ethyl sarin (isopropylethylphosphonofluoridate, GE), EDMP (ethyl-2-diisopropylaminoethylmethylphosphonate), DF (methylphosphonyl difluoride), Novichok Agents, GV (P[2-(dimethylamino)ethyl]-N,N-dimethylphosphonamidic fluoride), Gd42, Gd83, Tammelin Esters, fluorophosphocholines, phosphothiocholates, DFP, and insecticides (phenothiazines, organophosphates (dichorous, malathion, parathion, fenthion, amidon, paraoxon, chloropyrifos, systox, pyrophosphate, TOCP)). Victims of nerve agents may exhibit symptoms including, but not limited to, bradycardia, myosis, excessive salivation, vomiting, diarrhea, involuntary micturition, muscle fasciculation, initial depolarizing flaccid paralysis, spike discharges and convulsions, intermediate syndrome, neurotoxic esterase inhibition, and organophosphate-induced delayed neuropathy.

(B) "Blister Agents" refer to agents that are acid-forming compounds that damage the victim's skin and respiratory system resulting in burns and respiratory problems. Chemical agents within this category include, but are not limited to, sulfur mustards (1,2 bis(2-chloroethylthio)ethane (Sesquimustard, Q), 1,3 bis(2-chloroethylthio)-n-propane, 1,4-bis (2-chloroethylthio)-n-butane, 1,5-bis(2-chloroethylthio)-n-pentane, 2-Chloroethylchloromethylsulfide, Bis(2-chloroethyl)sulfide (HD), Bis(2-chloroethylthio) methane, Bis(2-chloroethylthiomethyl) ether, Bis(2-chloroethylthioethyl) ether, di-2'-chloroethylsulfide and combinations thereof (HT, HL, HQ)), nitrogen mustards (Bis(2-chloroethyl)ethylamine (HN1), Bis(2-chloroethyl)methylamine (HN2), Tris(2-chloroethyl)amine (HN3), 2-chloro-N-(2-chloroethyl)-N-methylethanamine-N-oxide hydrochloride, cyclophosphamide, chlorambucil, uramustine, melphalan), lewisites (2-Chlorovinyldichloroarsine, Bis(2-chlorovinyl) chloroarsine, Tris(2-chlorovinyl)arsine, dichloro(2-chlorovinyl)arsine), ethyldichloroarsine, methyldichloroarsine, phenyldichloroarsine, and phosgene oxime (dichloroformoxime). Victims of blister agents may exhibit symptoms including, but not limited to, erythema, edema, necrosis and vesicles, melanoderma, tracheobronchitis, bronchospasms, bronchial obstruction, hemorrhagic pulmonary edema, respiratory failure, bacterial pneumonia, eye erythema, lachrymation, discomfort of the eyes, severe pain in the eyes, dry eye, blepharospasm, iritis, blindness, nausea, vomiting, bone marrow suppression, lewisite shock, hepatic necrosis, and renal failure secondary to hypoperfusion.

(C) "Pulmonary Agents" refer to agents that are similar to blister agents but have a more pronounced effect on the respiratory system resulting in the respiratory system being flooded and the victim suffocating. Chemical agents within this category include, but are not limited to, adamsite, Acrolein, Bis(chloromethyl)ether, chlorine, Chloropicrin, diphosphogene, methyl chlorosulfate, stannic chloride, hydrogen chloride, nitrogen oxides, and phosgene. Victims of pulmonary agents may exhibit symptoms including, but not limited to, burning sensations (eyes, nasopharynx, oropharynx), profuse tearing, rhinorrhoea, coughing hoarseness, dyspnoea, odynophagia, conjunctivitis, corneal injury, naso-orophangyal injury/edema, respiratory distress due to inflammation of the glottic structures, secretions, and/or laryngospasms, acute respiratory syndromes, and reactive airway dysfunction syndrome.

(D) "Incapacitating agents" refer to agents that are less lethal and are intended largely to incapacitate through physiological or mental effects or both. A common class of incapacitating agents is lachrymatory agents, chemical agents that irritate the eyes causing tearing, pain, and even temporary blindness. Lachrymatory agents include, but are not limited to, a-chlorotoluene, benzyl bromide, Bromoacetone (BA), Bromobenzylcyanide (CA), Bromomethyl ethyl ketone, Capsaicin (OC), Chloracetophenone (CN), chloromethyl chloroformate, Dibenzoxazepine (CR), Ethyl iodoacetate, Ortho-chlorobenzylidene malonitrile (CS), Trichloromethyl chloroformate, and xylyl bromide. Additional incapacitating agents include, but are not limited to, 3-Quinuclidinyl benzilate (psychedelic; BZ), hydrocyanic acid (paralytic), diphenylchloroarsine (sternutatory; DA), diphenylcyanoarsine (DC), KOLOKOL-1 (fentanyl derivative), Datura stramonium, Hellborne, Belladonna, Hyoscyamus falezlez, indoles (lysergic acid diethylamide (LSD-25)), marijuana derivatives (DMHP), amphetamines, cocaine, caffeine, nicotine, strychnine, metrazole, barbiturates (methohexital), opioids, antipsychotics (haloperidol), benzodiazepines, fentanyl congeners, psilocybin, ibogaine, harmine, ectasy, PCP, atropine, scopolamine, oxybutynin, ditropan, anticholinergic antihistamines, benactyzine, and tranquilizers.

Many of the above noted chemicals have uses beyond their use as weapons and are used within manufacturing. Thus, the accidental or intentional release of these chemical agents from manufacturing or chemical plants will pose a risk to the employees of the plant as well as the populations living in the vicinity of these plants. Examples of toxic industrial manufacturing chemicals include, but are not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid, phosgene, phosphorous trichloride, sulfur dioxide, sulfuric acid, tungsten hexafluoride, acetone cyanohydrin, acrolein, acrylotrile, allyl alcohol, allyl amine, allyl chlorocarbonate, boron tribromide, carbon monoxide, carbonyl sulfide, chloroacetone, chloroacetylnitrile, chloro sulfonic acid, diketone, 1,2-dimethyl hydrazine, ethylene dibromide, hydrogen selenide, methane sulfonyl chloride, methyl bromide, methyl chloroformate, methyl chlorosilane, methyl hydrazine, methyl isocyanate, methyl mercapatan, nitrogen dioxide, phosphine, phosphorous oxychloride, phosphorous pentafluoride, selenium hexafluoride, silicone tetrafluoride, stiloine, sulfur trioxide, sulfuryl chloride, sulfuryl fluoride, tellurium hexafluoride, n-octyl mercaptan, titanium tetrachloride, trichloroacetyl chloride, trifluoroacetyl chloride, allyl isothiocyanate, arsenic trichloride, bromine, bromine chloride, bromine penta fluoride, bromine trifluoride, carbonyl fluoride, chlorine penta fluoride, chlorine trifluoride, chloroacetylaldehyde, chloroacetylchloride, crotonaldehyde, cyanogens chloride, dimethyl sulfate, diphenylmethane-4,4'-diisocyanate, ethyl chloroformate, ethyl chlorothioformate, ethyl phosphonothioic dichloride, ethyl phosphonic dichloride, ethyleneimine, hexachlorocyclopentadiene, hydrogen iodine, iron pentcarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl isocyanate, tert-butyl isocyanate, tetraethyl lead, tetraethyl pyrophosphate, tetra methyl lead, toluene 2,4-diisocyanate, and toluene 2,6-diisocyanate.

(xii) As used herein, an "effective amount" includes that amount of a peptide sufficient to modulate any disease or disorder associated with tissue damage or the damage associated with an effect, or a symptom of the disease or disorder, for example to inhibit, suppress, or moderate the deleterious effects of the body's response to the disease or disorder associated with the tissue damage including, but not limited to, the body's response to cancer, inflammation, or exposure to toxic agents. Additionally, an "effective amount" includes the amount of the peptide sufficient to mitigate, ameliorate, diminish or prevent any disease or disorder associated with tissue damage or provide a therapeutic benefit in a patient afflicted with a disease or disorder associated with tissue damage.

(xiii) "Excitable tissue" means tissue that contains excitable cells. Excitable cells are cells that respond actively to an electric stimulus and have an electrical charge differential across their cellular membranes. Excitable cells are generally capable of undergoing an action potential. Such cells typically express channels, such as voltage-gated, ligandgated, and stretch channels, which allow flow of ions (potassium, sodium, calcium, chloride, etc.) across the membrane. Excitable tissue includes neuronal tissue, muscle tissue, and glandular tissue. Excitable tissue includes, but is not limited to, neuronal tissues such as tissue of the peripheral nervous system (ear and retina) and central nervous system (brain and spinal cord); cardiovascular tissue such as the cells of the heart and associated nerves; and glandular tissue such as the pancreas where T-type calcium channels along with cell-to-cell gap junctions participate in secretion of insulin. An exemplary list of excitable tissues includes organs and tissues that include nerves, skeletal muscle, smooth muscle, cardiac muscle, uterus, central nervous system, spinal cord, brain, retina, olfactory system, auditory system, etc.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

(xv) The term "inflammatory conditions" as used herein refers to various diseases or traumas, whether mechanically or chemically induced, that have an inflammatory component. It includes conditions giving rise to inflammation in one or more organs or tissues including, but not limited to, the brain, spinal cord, connective tissue, heart, lung, kidney, urinary tract, pancreas, eyes and prostate. Non-limiting examples of such conditions include, but are not limited to, appendicitis, blepharitis, bronchitis, bursitis, cervicitis, cholangitis, cholecystitis, chorioamnionitis, conjunctivitis, cystitis, dacryoadenitis, dermatitis, endocarditis, endometritis, epicondylitis, epididymitis, fibrositis, gastritis, gingivitis, glossitis, hidradenitis suppurativa, iritis, laryngitis, mastitis, myocarditis, myositis, nephritis, omphalitis, oophoritis, orchitis, osteitis, otitis, parotitis, pericarditis, peritonitis, pharyngitis, pleuritis, phlebitis, pneumonitis (pneumonia), prostatitis, pyelonephritis, rhinitis, salpingitis, sinusitis, stomatitis, synovitis, tonsillitis, uveitis, urethritis, vaginitis, vulvitis, asthma, systemic lupus erythematosus, myasthenia gravis, tendonitis, angiitis, chronic bronchitis, pancreatitis, osteomyelitis, arthritis (rheumatoid and psoriatic), glomerulonephritis, optic neuritis, temporal arteritis, encephalitis, meningitis, traverse myelitis, dermatomyositis, polymyositis, necrotizing fasciitis, hepatitis, necrotizing entercolitis, pelvic inflammatory disease, inflammatory bowel disease (colitis, e.g., ulcerative colitis, Crohn's disease, ileitis, and enteritis), proctitis, vasculitis, vascular stenosis, restenosis, hypotension, Type-1 diabetes, Kawasaki disease, Decum's disease, chronic obstructive pulmonary disease, psoriasis, artherosclerosis, scleroderma, Sjogren's syndrome, mixed connective tissue disease, rosacea, gastric ulcers, duodenal ulcers, Alzheimer's disease, adult onset Still's disease, acute retinal pigment epitheliitis, Tietze's syndrome, Bechçet's disease, white dot syndrome (acute posterior multifocal placoid pigment epitheliopathy, serpiginous choroiditis, birdshot chorioretinopathy, multifocal choroiditis with panuveitis, diffuse subretinal fibrosis syndrome, punctuate inner choroidopathy, multiple evanescent white dot syndrome, and diffuse unilateral subacute neuroretinitis), granuloma annulare, irritable bowel syndrome, Crohn's disease, celiac disease, gastroenteritis, Graves' disease, multiple sclerosis, Dupuytren's contracture, graft rejection diseases (including allograft rejection and graft-v-host disease), e.g. skin graft rejection, solid organ transplant rejection, bone marrow transplant rejection, inflammatory dermatoses, viral cutaneous pathologies such as those derived from human papilloma virus, HIV, or RLV infection, bacterial, fungal and or other parasital cutaneous pathologies, cutaneous lupus erythematosus, and Hyper IgG4 disease. Further "Inflammatory condition" may refer to inflammation resulting from ischemic or non-ischemic conditions, including but not limited to, blunt trauma, contusions, allergies and allergic diseases, rheumatic disease (childhood arthritis, rheumatoid arthritis, Churg-Strauss syndrome, fibromyalgia, giant cell (temporal) arteritis, gout, Henoch-Schoenlin purpura, hypersensitivity vasculitis, ankylosing spondylitis, capsulitis, rheumatic fever, rheumatic heart disease, systemic lupus erythematosus, polymyalgia rheumatica, osteoarthritis (hand, hip, knee, etc.) polyarteritis nodosa, Reiter's syndrome, sports related injuries (runner's knee, tennis elbow, frozen shoulder, Achilles tendonitis, plantar fasciitis, bursitis, Osgood-Schlatter disease), repetitive stress injuries (cumulative trauma diseases, focal dystonia, carpal tunnel syndrome, intersection syndrome, reflex sympathetic dystrophy syndrome, stenosing tenosynovitis (De Quervain's syndrome, trigger finger/trigger thumb), thoracic outlet syndrome, tendonitis, tenosynovitis, radial tunnel syndrome, Raynaud's disease, ganglion, gamer's thumb, Wii-itis, etc.) infections including viral, fungal and bacterial. The "inflammatory condition" may be acute or chronic.

(xvi) An "isolated" or "purified" peptide is substantially free of cellular material or other contaminating proteins from the cell or tissue source from which the protein or peptide is derived, or substantially free of chemical precursors or other chemicals when chemically synthesized. The language "substantially free of cellular material" includes preparations of a peptide in which the peptide is separated from cellular components of the cells from which it is isolated or recombinantly produced. Thus, a peptide that is substantially free of cellular material includes preparations of peptides having less than about 30%, 20%, 10%, or 5% (by dry weight) of heterologous protein (also referred to herein as a "contaminating protein"). When the peptide is recombinantly produced, it can also be substantially free of culture medium, i.e., culture medium represents less than about 20%, 10%, or 5% of the volume of the protein preparation. When the peptide is produced by chemical synthesis, it can be substantially free of chemical precursors or other chemicals, i.e., it is separated from chemical precursors or other chemicals which are involved in the synthesis of the protein. Accordingly such preparations of the peptide have less than about 30%, 20%, 10%, 5% (by dry weight) of chemical precursors or compounds other than the peptide of interest. In one embodiment, peptides provided herein are isolated or purified.

(xvii) An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding a peptide provided herein is isolated or purified.

(xviii) As used herein, the term "management" includes the provision of one or more beneficial side effects that a patient derives from a peptide which, in one embodiment, does not reverse the damage, effects or symptoms of a a disease or disorder associated with tissue damage. In certain embodiments, a patient is administered a peptide to "manage" the symptoms of a disease or disorder associated with tissue damage so as to prevent the progression or worsening of the symptoms.

(xix) The terms "modulate," "modulations" and the like refer to the ability of a compound to increase or decrease the function and/or expression of mediators of the body's response to a disease or disorder associated with tissue damage, including transcription of regulatory activity and/or protein binding. Modulation, as described herein, includes the inhibition, antagonism, partial antagonism, activation, agonism or partial agonism of a function or characteristic associated with the mediator, either directly or indirectly, and/or the upregulation or downregulation of the expression of the mediator. In one embodiment, the modulation is direct, and the modulation can occur through an inhibitor or antagonist of the mediator, a compound that binds to, partially or totally blocks stimulation, decreases, prevents, inhibits, delays activation, inactivates, desensitizes, or downregulates signal transduction. The ability of a particular peptide useful in the method provided herein to inhibit the function of a mediator can be demonstrated in a biochemical assay, e.g. binding assay, cell based assay, e.g. transient transfection assay, or in vivo assay, e.g. animal model of neuronal injury, cancer, inflammation, or chemical or radiation injury such as a rat or murine model.

(xx) As used herein in reference to a structure within a peptide, the term "motif" refers either to a set of consecutive amino acids within the amino acid sequence of the peptide chain and/or to a set of linearly or spatially adjacent amino acids within the secondary and/or tertiary structure of said peptide. Because the motif may be formed all or in part as a result of protein folding, amino acids that are adjacent in the described motif may be separated by 0, 1 or more, 5 or more, 10 or more, 15 or more or 20 or more amino acids within the linear amino acid sequence of the peptide.

(xxi) As used herein, the terms "peptide," "polypeptide" and "protein" are used interchangeably and in their broadest sense to refer to constrained (that is, having some element of structure as, for example, the presence of amino acids which initiate a β turn or β pleated sheet, or for example, cyclized by the presence of disulfide bonded Cys residues) or unconstrained (e.g., linear) amino acid sequences. In certain embodiments, the peptide provided herein consists of less than 30 amino acids. However, upon reading the instant disclosure, the skilled artisan will recognize that it is not the length of a particular peptide but its ability to bind a tissue protective receptor complex and/or compete with the binding of a peptide described herein that distinguishes the peptides useful in the method provided herein. The terms "peptide," "polypeptide," and "protein" also refer to compounds containing amino acid equivalents or other non-amino acid groups, while still retaining the desired functional activity of a peptide or protein. Peptide equivalents can differ from conventional peptides by the replacement of one or more amino acids with related organic acids (such as PABA), amino acid equivalents or the like or the substitution or modification of side chains or functional groups.

(xxii) The term "preventing the damages, effects or symptoms of a disease or disorder associated with tissue damage" means delaying the onset, hindering the progress, hindering the appearance, protection against, inhibiting or eliminating the emergence, or reducing the incidence, of such damages, effects or symptoms. Use of the term "prevention" is not meant to imply that all patients in a patient population administered a preventative therapy will never be affected by or develop symptoms in response to the disease or disorder associated with tissue damage targeted for prevention, but rather that the patient population will exhibit a reduction in the damage, effects, or symptoms of the disease or disorder. For example, many flu vaccines are not 100% effective at preventing flu in those administered the vaccine. One skilled in the art can readily identify patients and situations for whom preventative therapy would be beneficial, such as, but not limited to, individuals about to engage in activities that may expose them to various toxic agents or traumas (e.g., soldiers engaging in military operations, chemical or food processing workers, emergency personnel or first responders, etc.), or individuals that may be subjected to exposure to a toxic agent (e.g., individuals living in the vicinity of chemical, nuclear, or manufacturing facilities, or individuals under threat of military or terrorist attack).

(xxiii) As used herein, a "prophylactically effective amount" refers to that amount of a peptide sufficient to result in the prevention of the damage, effects or symptoms resulting from a disease or disorder associated with tissue damage. A prophylactically effective amount can refer to the amount of a peptide sufficient to prevent the damage, effects or symptoms resulting from a disease or disorder associated with tissue damage. Further, a prophylactically effective amount with respect to another prophylactic agent means that amount of that prophylactic agent in combination with a peptide that provides a prophylactic benefit in the prevention of damage, effects or symptoms resulting from a disease or disorder associated with tissue damage. Used in connection with an amount of a peptide, the term "prophylactically effective amount" can encompass an amount that improves overall prophylaxis or enhances the prophylactic efficacy of or provides a synergistic affect with another prophylactic agent.

(xxiv) The term "neoplasm" refers to abnormal growths that lack the malignant properties of cancerous tumors, and are generally mild and non-progressive tumors. Neoplasms, include but are not limited to moles, uterine fibroids, thyroid adenomas, adrenocortical adenomas, pituitary adenomas, and teratomas.

(xxv) The term "radiation agent" as used herein means any radioactive material that may kill or injure a subject, and may be used to cause disruption upon a city or nation. Exposure to a radiation agent may occur through deployment of a weapon (nuclear bomb (fission, fusion, neutron, boosted fission, or salted bombs), shells containing depleted uranium), terrorist device ("dirty bomb"), or fallout resulting from the detonation of a nuclear weapon or failure of a nuclear plant. Radioactive agents may include, but are not limited to, $^{137}Cs$, $^{60}Co$, $^{241}Am$, $^{252}Cf$, $^{192}Ir$, $^{238}Pu$, $^{90}Sr$, $^{226}Ra$, $^{91}Sr$, $^{92}Sr$, $^{95}Sr$, $^{99}Mo$, $^{106}Ru$, $^{131}Sb$, $^{132}Te$, $^{139}Te$, $^{140}Ba$, $^{141}La$, $^{144}Ce$, $^{233}U$, $^{235}U$, $^{238}U$, $^{228}P$, $^{229}P$, $^{230}P$, $^{231}P$, $^{232}P$, $^{233}P$, $^{234}P$, $^{235}P$, $^{236}P$, $^{237}P$, $^{238}P$, $^{239}P$, $^{240}P$, $^{241}P$, $^{242}P$, $^{243}P$, $^{244}P$, $^{245}P$, $^{246}P$, $^{247}P$, and $^{131}I$. Exposure to the radioactive agents can result in carcinogenesis, sterilization, cataract formation, radiodermatitis, beta burns, gamma burns, loss of cells (in particular bone marrow, digestive tract cells), damage to the hematopoietic, gastrointestinal, central nervous, cardiovascular, skin, and/or reproductive systems, acute radiation syndrome, chronic radiation syndrome, and cutaneous radiation syndrome. Acute radiation syndrome generally results from large doses of radiation to a subject's body occurring in a short period of time. The syndrome has a predictable course starting with a feeling of nausea, vomiting, general illness and fatigue, immune system depression, loss of hair, uncontrollable bleeding (mouth, under the skin, kidneys), massive diarrhea, delirium, coma and death. Cutaneous radiation syndrome is a subset of acute radiation syndrome and refers to radiations effects on the skin, which include, but are not limited to, inflammation, erythema, dry or moist desquamation, hair loss, blistering, reddening, ulceration, damage to sebaceous and sweat glands, atrophy, fibrosis, decreased or increased skin pigmentation, and necrosis.

(xxvi) As used herein, the terms "subject," "patient" and "victim" are used interchangeably. As used herein, the terms "subject" and "subjects" refer to an animal, for example a mammal including a non-primate (e.g., a cow, pig, horse, cat, dog, rat, and mouse) and a primate (e.g., a monkey, an ape, or a human).

(xxvii) As used herein, the term "syndromes associated with neoplasms or cancers" refers to syndromes resulting from the direct action of the tumors through "mass effect" (compression of vital organs due to tumor) or "functional tumors" (overproduction of hormones by organ afflicted with tumor). Such syndromes include, but are not limited to, Beckwith-Wiedmann syndrome, SBLA syndrome, Li-Fraumeni syndrome, Vasoproliferation, Familial Adenomatous Polyposis syndrome (Gardner syndrome), Hereditary Non-polyposis Colorectal Cancer, Turcot syndrome, Cowden syndrome, Carney Triad syndrome, Multiple Endocrine Neoplasia syndromes (Wermer (MEN-1), Sipple (MEN-2a, MEN-2b), Von Hipple-Lindau syndrome, Cushing's syndrome, Addison's syndrome, Verner Morrison syndrome, Zollinger-Ellison syndrome, WDHA syndrome, Pancreatic Cholera, Isaac's syndrome, Rippling muscle syndrome, Stiffman syndrome, Paraneoplastic Ataxia, Yo syndrome, Tr syndrome, Hu syndrome, CV-2 syndrome, CRMP-5 syndromes, Opsoclonus/Myoclonus, Ma syndromes, Morvan's fibrillary chorea, Bannayan-Riley-Runalcaba syndrome, Peutz-Jegher syndrome, Muir-Torre syndrome, Hirschsprung disease, Lynch syndrome, Lambert-Eaton Myastenic syndrome, Myasthenia Gravis, Neuromyotonia, Paraneoplastic Cerebellar Degeneration, Paraneoplastic Limbic Encephalitis, Sweets syndrome, Birt-Hogg-Dube syndrome, Nevoid Basal Cell Carcinoma syndrome, Generalized Basaloid Follicular syndrome, Hamartoma syndrome, Bazex syndrome, Brooke Spiegler syndrome, Familial Cylindromatosis, Multiple Familial Trichoepitheliomas, Androgen Deprivation syndrome, Therapy Related Myelodysplastic syndrome, Somnolence syndrome, Gulf War syndrome, and Somatostatinoma syndrome.

(xxviii) As used herein, the term "tissue protective activity" or "tissue protection" refers to the effect of inhibiting or delaying damage or death of a cell, tissue, or organ. Unless otherwise noted, the "delay" in damage or death of a cell, tissue or organ is evaluated relative to a control condition in the absence of a peptide provided herein. Tissue protective activity is specific to tissue, cells, and/or organs expressing a tissue protective receptor complex (i.e., a responsive tissue cell, and/or organ, respectively), such as, but not limited to, the tissues of the central nervous system. In specific embodiments, the responsive cells are not erythrocyte progenitor cells.

(xxix) The term "tissue protective receptor complex" as used herein means a complex comprising at least one erythropoietin receptor subunit and at least one beta common receptor subunit. The tissue protective receptor complex may contain multiple erythropoietin receptor subunits and/or beta common receptor subunits, as well as other types of receptors or proteins. See WO 2004/096148, which is hereby incorporated by reference herein in its entirety.

(xxx) The term "toxic agent" as used herein refers to the biological, chemical and radiation agents mentioned above.

(xxxi) To determine the percent identity of two amino acid sequences, the sequences are aligned for optimal comparison purposes. The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical overlapping positions× 100/total number of positions). In one embodiment, the two sequences are the same length. In an alternate embodiment, the sequences are of different length and, accordingly, the percent identity refers to a comparison of the shorter sequence to a portion of the longer sequence, wherein said portion is the same length as said shorter sequence.

(xxxii) As used herein, the term "treatment" includes the elimination, reduction, management or control of damage, effects or symptoms resulting from a disease or disorder associated with tissue damage or the damage associated with an effect, or a symptom of the disease or disorder.

5. BRIEF DESCRIPTION OF THE FIGURES

FIG. 1 shows the effects of a peptide embodied herein on a spared nerve model of neuropathic pain in the rat. Squares indicate animals receiving vehicle (control), whereas triangles indicate animals receiving GDKA (SEQ ID NO: 3) peptide, dark circles indicate animals receiving GDKARYEREM (SEQ ID NO: 1) peptide, and light grey circles indicate animals receiving a positive control. The peptide of SEQ ID NO: 282 from U.S. Pat. No. 8,853,358 was used as the positive control.

Figure 2:
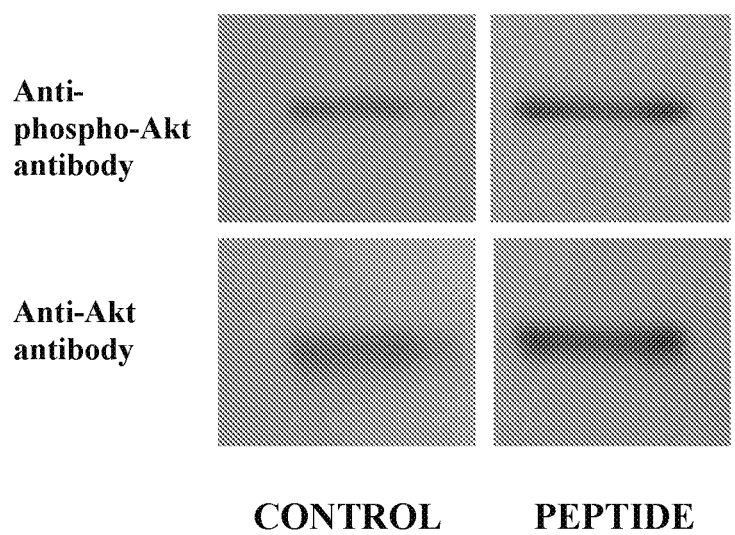

FIG. 2 shows the activation of phosphorylation of Akt by GDKA (SEQ ID NO: 3) peptide.

Figure 3:
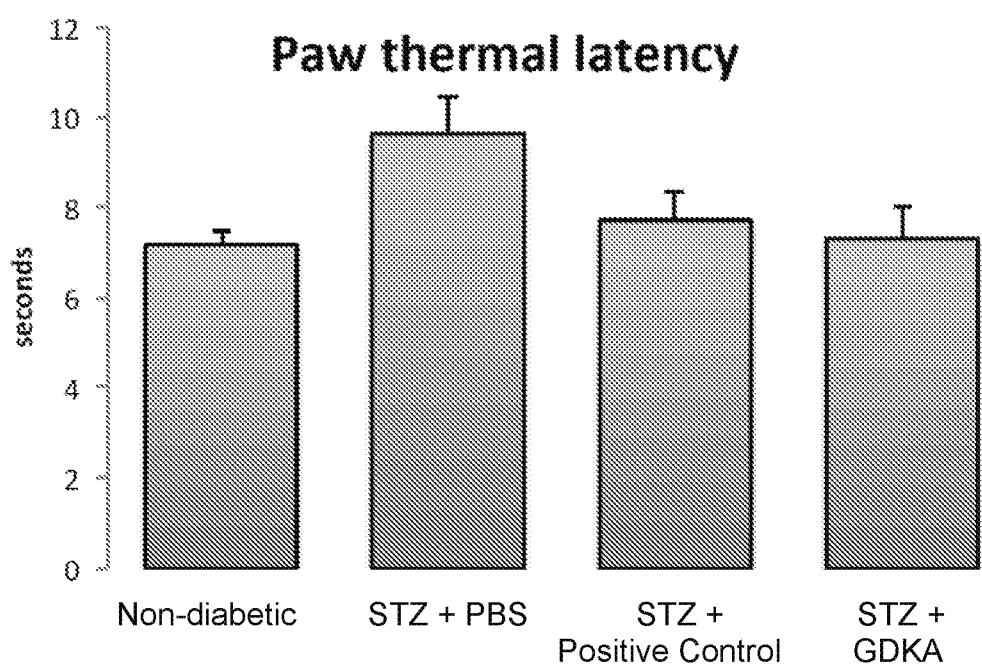

FIG. 3 shows the protective effects of a peptide embodied herein on a diabetic neuropathy mouse model. Mice receiving GDKA (SEQ ID NO:3) peptide were compared with mice treated with PBS in the diabetic neuropathy model. Non-diabetic mice were included as a control. The tissue-protective peptide of SEQ ID NO: 282 from U.S. Pat. No. 8,853,358 was used as the positive control.

6. DETAILED DESCRIPTION

6.1 Isolated Peptides

Provided herein is a method of modulating the effects of the body's response to a disease or disorder associated with tissue damage. Further, provided herein is a method of preventing, treating, ameliorating, or managing damage, effects or symptoms in a patient afflicted with a disease or disorder associated with tissue damage by administering a peptide or peptide analog that shares a consensus sequence of GDKA (SEQ ID NO: 3). In certain embodiments, the peptide consists of the amino acid sequence GDKARYEREM (SEQ ID NO:1). In another embodiment, the peptide comprises the amino acid sequence GDKARYEREM (SEQ ID NO:1). In another embodiment, the peptide consists of the amino acid sequence GDKARYEREA (SEQ ID NO:2). In another embodiment, the peptide comprises the amino acid sequence GDKARYEREA (SEQ ID NO:2). In yet another embodiment, the peptide consists of the amino acid sequence GDKA (SEQ ID NO:3). In still yet another embodiment, the peptide comprises the amino acid sequence GDKA (SEQ ID NO:3). In one embodiment, the peptide used in the method is tissue protective, neuroprotective, neuritogenic, or anti-apoptotic.

A peptide provided herein can comprise the amino acid sequence of GDKARYEREM (SEQ ID NO:1), GDKARY- EREA (SEQ ID NO:2) or GDKA (SEQ ID NO: 3), wherein the peptide contains from 5 amino acids to up to about 30 amino acids, wherein the amino acid sequence is located at the N-terminus, C-terminus or any other location within the peptide. Furthermore, a conservative or non-conservative amino acid substitution can be made at one or more amino acid residues in the peptide, or a substitution with an amino acid equivalent. Both conservative and non-conservative substitutions can be made. In another embodiment, more than one substitution can be made. Accordingly, in some embodiments, a peptide provided herein includes a peptide having one amino acid residue replaced with a conservative substitution, a non-conservative substitution, or an amino acid equivalent. In a specific embodiment, a peptide provided herein having the amino acid sequence GDKARY-EREM (SEQ ID NO:1), GDKARYEREA (SEQ ID NO:2) or GDKA (SEQ ID NO: 3) includes an amino acid sequence with one conservative substitution. A peptide having any one of the substitutions described herein includes a peptide that maintains its tissue protective activity as described herein, which can be assayed using one or more of the methods described herein for assaying tissue protective activity.

Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar (hydrophobic)=cysteine, alanine, valine, leucine, isoleucine, proline, phenylalanine, methionine, tryptophan, glycine, tyrosine; and (4) uncharged polar=asparagine, glutamine, serine, threonine. Non-polar may be subdivided into: strongly hydrophobic=alanine, valine, leucine, isoleucine, methionine, phenylalanine and moderately hydrophobic=glycine, proline, cysteine, tyrosine, tryptophan. In alternative fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 4th ed., Ed. by L. Stryer, WH Freeman and Co., 1995, which is incorporated by reference herein in its entirety). Amino acid equivalent refers to compounds that depart from the structure of the naturally occurring amino acids, but which have substantially the structure of an amino acid, such that they can be substituted within a peptide, which retains its biological activity despite the substitution. Thus, for example, amino acid equivalents can include amino acids having side chain modifications or substitutions, and also include related organic acids, amides or the like.

Thus, one of ordinary skill in the art would recognize that the isolated peptide can have at least 90%, at least 85%, at least 80%, at least 75%, at least 70%, at least 65%, at least 60%, at least 55%, at least 50%, at least 45%, v 40%, at least 35%, at least 30%, or at least 20 percent sequence identity with the amino acid sequence of GDKARYEREM (SEQ ID NO:1), GDKARYEREA (SEQ ID NO:2) or GDKA (SEQ ID NO: 3).

Not wishing to be bound by any particular theory, for tissue protection, a pair of charged amino acids in the peptide can be spatially oriented such that the carbamyl carbons are about 3 angstroms (Å) to about 5 Å apart, in one embodiment about 4 Å to about 5 Å apart, and in one embodiment about 4.4 Å to about 4.8 Å apart. This can be accomplished in a number of ways, for example, by adjacent charged amino acids in a simple linear peptide or for peptides that can form an alpha helix, charged amino acids separated by an intervening amino acid residue. It is to be noted that tertiary structure (e.g., an alpha helix in amphipathic peptides) can also be imparted when the peptide is within a specific microenvironment, such as at the extracellular-cell surface membrane interface (see, Segrest, 1990, Proteins 8:103-117, hereby incorporated by reference in its entirety).

Further, tissue protective activity is predicted for peptides that contain pairs of charged amino acids such that the charged side-chains (either positive or negative, or two negatives) be confined spatially to within about 6.5 Å to about 9 Å of each other. This can be provided for in an alpha helix by the charged pair being separated by one or two amino acids, which will provide for the charges to be more or less on the same side of the helix with the required about 6.5 Å to about 9 Å separation. One skilled in the art can devise a tertiary structure for the peptide that is generally required to obtain the appropriate three dimensional location of the charged amino acids, as well as the design of small molecules to mimic the charge separation within the peptide.

The spatial distances between the carbamyl carbons of any two amino acids or between the side chains of any two amino acids can be deduced by any method known in the art or described herein. For example, where the three-dimensional structure of the protein is known, the charge separation of two side chains or the spatial distance between two carbamyl carbons within a portion of interest of said protein can be calculated based on the published, or otherwise art-accepted, three-dimensional coordinates of the amino acid residues in said portion of interest. Where the three-dimensional structure of the protein and, therefore, the portion of interest is unknown, or wherein a fully synthetic peptide is constructed based on the teachings herein, whose three dimensional structure is unknown, the charge separation of two side chains or the spatial distance between two carbamyl carbons within said peptide can be estimated using the three-dimensional structure predicted by protein modeling software as is known in the art. Non-limiting examples of such software are MOE' by Chemical Computing Group (Quebec, Canada) and Modeler by Accelrys (San Diego, Calif.). Similarly such predictive software, available from the above-noted companies as well, is also known in the art for the design of small molecules as and, accordingly, one of ordinary skill in the art, based upon the teachings herein, would be able to make small molecules that emulate the disclosed structural motifs.

6.2 Chimeras

"Chimeric" peptides include linear amino acid sequences that incorporate an amino acid sequence provided herein, such as, but not limited to, GDKARYEREM (SEQ ID NO:1), GDKARYEREA (SEQ ID NO:2) or GDKA (SEQ ID NO: 3). Chimeric peptides useful in the current methods and compositions can consist of combining structural elements of separate amino acid sequences into a single peptide. In other words, a chimeric peptide may be comprised of an amino acid sequence provided herein that is adjacent to structural/functional elements. For example, the potency of the current peptides may be increased by attaching an amphipathic peptide helix.

Amphipathic peptide helices are well known in the art, e.g. from peptides that signal through the Class B G-protein coupled receptors (e.g., Segrest et al., 1990, Proteins 8:103, hereby incorporated by reference in its entirety), serving to localize the peptide ligand to the cell membrane. Examples of such helices include, but are not limited to, the highly hydrophobic regions from: calcitonin (Peptide A:ALSIL-VLLQAGS, SEQ ID NO:4); corticotropin releasing hormone (Peptide B:VALLPCPPCRA, SEQ ID NO:5); beta endorphin (Peptide C:NAIIKNAYKKG, SEQ ID NO:6); glucagon (Peptide D:GSWQRSLQDTE, SEQ ID NO:7); secretin (Peptide E:GGSAARPAPP, SEQ ID NO:8); vasointestinal peptide (Peptide F:NALAENDTPYY, SEQ ID NO:9); neuropeptide Y (Peptide G:GALAEAYPSKP, SEQ ID NO:10); gonadotropin releasing hormone (Peptide H:GCSSQHWSYGL, SEQ ID NO:11); parathyroid hormone (Peptide I:VMIVMLAICFL, SEQ ID NO:12); pancreatic polypeptide (Peptide J:LRRYINMLTRP, SEQ ID NO:13); and calcitonin gene related peptide (Peptide K:LALSILVLYQA, SEQ ID NO:14) (disclosed in Grace et al., 2004, PNAS 101:12836, hereby incorporated by reference in its entirety). For example, a chimeric peptide useful in the methods provided herein may be made from a peptide with the GDKA (SEQ ID NO:3) joined at the carboxy terminus to the amphipathic helix of pancreatic polypeptide (Peptide J:LRRYINMLTRP, SEQ ID NO:13) for a chimeric peptide (GDKALRRYINMLTRP, SEQ ID NO:14). Further modifications may be made to the carboxy terminus of the amphipathic helix without affecting its tissue protective properties. Thus, a further example of a peptide useful in the treatment of a disease or disorder associated with tissue damage or damage associated with an effect, or a symptom of the disease or disorder is generated by replacing the terminal Pro of the above chimeric peptide with the sequence TR (GDKALRRYINMLTRTR, SEQ ID NO:15).

In certain embodiments, a linking arm will be present between the fused peptides to provide for flexibility so that the joined peptides can assume the proper structural orientation to bind with the tissue protective receptor complex. Such fusion peptides may have a synergistic effect, obtaining a greater tissue protective effect jointly as opposed to individually possibly through enhanced binding with the tissue protective receptor complex or increased biological half life.

One of ordinary skill in the art will recognize the benefit of combining various desired structural elements in to a single peptide for maximizing the effectiveness of such compounds in the method of preventing, treating, ameliorating or managing damages, effects, or symptoms resulting from exposure to a toxic agent in accordance with the disclosure herein. Such chimeras may comprise amino acids peptides, and non-amino acid elements, such as linkers or bridging atoms or moieties.

6.3 Fusion Peptides

Further contemplated herein are that two or more of the above noted peptides, fragment derived or chimera, may be linked to a related or unrelated protein such as albumin. Such fusion peptides may be generated in order to achieve synergistic benefits, increase the circulating half-life of the peptide, or increase the ability of the peptide to penetrate endothelial barriers, such as the blood-brain barrier, blood-retina barrier, etc., or vice versa, i.e. to act as a transport mechanism.

6.4 Manufacture of Peptides

Peptides useful in the method provided herein may be made using recombinant or synthetic techniques well known in the art. In particular, solid phase protein synthesis is well suited to the relatively short length of the peptides and may provide greater yields with more consistent results. Additionally, the solid phase protein synthesis may provide additional flexibility regarding the manufacture of the peptides. For example, desired chemical modifications may be incorporated into the peptide at the synthesis stage: homocitrulline could be used in the synthesis of the peptide as opposed to lysine, thereby obviating the need to carbamylate the peptide following synthesis or amino acids with protected functional groups may be left on the peptide during synthesis.

Synthesis

The isolated peptides and peptide analogs useful in a method provided herein may be prepared using conventional step-wise solution or solid phase synthesis (see, e.g., Merrifield, R. B., 1963, *J. Am. Chem. Soc.* 85:2149-2154; Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides and peptide analogs useful in a method provided herein may be prepared by way of segment condensation, as described, for example, in Liu et al., 1996, Tetrahedron Lett. 37(7):933-936; Baca, et al., 1995, *J. Am. Chem. Soc.* 117:1881-1887; Tam et al., 1995, *Int. J. Peptide Protein Res.* 45:209-216; Schnolzer and Kent, 1992, *Science* 256:221-225; Liu and Tam, 1994, *J. Am. Chem. Soc.* 116(10):4149-4153; Liu and Tam, 1994, *Proc. Natl. Acad. Sci. USA* 91:6584-6588; Yamashiro and Li, 1988, *Int. J. Peptide Protein Res.* 31:322-334). This is particularly the case with Gly (G) containing peptides. Other methods useful for synthesizing the peptides and peptide analogs provided herein are described in Nakagawa et al., 1985, *J. Am. Chem. Soc.* 107:7087-7092.

Recombinant Techniques

A variety of host-expression vector systems may be utilized to produce the peptides and peptide analogues. Such host-expression systems represent vehicles by which the peptide of interest may be produced and subsequently purified, but also represent cells that may, when transformed or transfected with the appropriate nucleotide coding sequences, exhibit the modified erythropoietin gene product in situ. These include but are not limited to, bacteria, insect, plant, mammalian, including human host systems, such as, but not limited to, insect cell systems infected with recombinant virus expression vectors (e.g., baculovirus) containing the peptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing erythropoietin-related molecule coding sequences; or mammalian cell systems, including human cell systems, e.g., HT1080, COS, CHO, BHK, 293, 3T3, PERC6 harboring recombinant expression constructs containing promoters derived from the genome of mammalian cells, e.g., metallothionein promoter, or from mammalian viruses, e.g., the adenovirus late promoter; the vaccinia virus 7.5K promoter.

In addition, a host cell strain may be chosen that modulates the expression of the inserted sequences, or modifies and processes the gene product in the specific fashion desired. Such modifications and processing of protein products may be important for the function of the protein. As known to those of ordinary skill in the art, different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is contemplated. For example, cell lines that stably express the recombinant tissue protective cytokine-related molecule gene product may be engineered. Rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the tissue-protective product.

Further Modifications

In certain embodiments, a peptide provided herein consists of the amino acid sequence of GDKARYEREM (SEQ ID NO:1), GDKARYEREA (SEQ ID NO:2), or GDKA (SEQ ID NO:3) and carries a chemical modification. In more specific embodiments, the chemical modification is a modification of a peptide bond. In certain more specific embodiments, the chemical modification is a modification of a side chain of an amino acid of the peptide. Specifically, the side chain of the first, second, third, fourth, fifth, sixth, seventh, eighth, ninth, and tenth, amino acid, up to any one of the amino acids of the peptide provided herein is modified. In some embodiments, the amino terminus of a peptide provided herein is modified. Alternatively or in addition, in some embodiments, the carboxyl terminus of a peptide provided herein is modified. In some embodiments, the chemical modification is a modification described herein, including, but not limited to, a modification resulting in a non-naturally occurring amino acid, carbamylation, acetylation, succinylation, guanidination, nitration, trinitrophenylation, amidination, or addition of a polymer (e.g., polyethylene glycol). A peptide having any one of the modifications described herein includes a peptide that maintains its tissue protective activity as described herein, which can be assayed using one or more of the methods described herein for assaying tissue protective activity.

Peptides with additional modifications can also be used in a method provided herein for preventing, treating, ameliorating or managing a disease or disorder associated with tissue damage or damage associated with an effect, or a symptom of the disease or disorder. For example, the peptides provided herein may be synthesized with one or more (D)-amino acids. The choice of including an (L)- or (D)-amino acid into a peptide provided herein depends, in part, upon the desired characteristics of the peptide. For example, the incorporation of one or more (D)-amino acids can confer increasing stability on the peptide in vitro or in vivo. The incorporation of one or more (D)-amino acids can also increase or decrease the binding activity of the peptide as determined, for example, using the bioassays described herein, or other methods well known in the art.

Replacement of all or part of a sequence of (L)-amino acids by the respective sequence of enantiomeric (D)-amino acids renders an optically isomeric structure in the respective part of the peptide chain. Inversion of the sequence of all or part of a sequence of (L)-amino acids renders retro-analogues of the peptide. Combination of the enantiomeric (L to D, or D to L) replacement and inversion of the sequence renders retro-inverso-analogues of the peptide. It is known to those skilled in the art that enantiomeric peptides, their retro-analogues, and their retro-inverso-analogues maintain significant topological relationship to the parent peptide, and especially high degree of resemblance is often obtained for the parent and its retro-inverso-analogues. This relationship and resemblance can be reflected in biochemical properties of the peptides, especially high degrees of binding of the respective peptides and analogs to a receptor protein. The synthesis of the properties of retro-inverso analogues of peptides have been discussed for example in Methods of Organic Chemistry (Houben-Weyl), Synthesis of Peptides and Peptidomimetics—Workbench Edition Volume E22c (Editor-in-chief Goodman M.) 2004 (George Thieme Verlag Stuttgart, New York), and in references cited therein, all of which are hereby incorporated by reference herein in their entireties.

Amino acid "modification" refers to the alteration of a naturally occurring amino acid to produce a non-naturally occurring amino acid. Derivatives of the peptides provided herein with non-naturally occurring amino acids can be created by chemical synthesis or by site specific incorporation of unnatural amino acids into peptides during biosynthesis, as described in Christopher J. Noren, Spencer J. Anthony-Cahill, Michael C. Griffith, Peter G. Schultz, 1989 Science, 244:182-188, hereby incorporated by reference herein in its entirety. Non-limiting examples of non-naturally occurring peptides include 2-thienylalanine, allylglycine, 3-methylphenylalanine, 3-pyridylalanine, 4-thiazolylalanine, 4,4'-biphenylalanine, 4-aminomethylphenylalanine, 4-fluorophenylanaline, 3,4-dichlorophenylalanine, pipecolic acid, beta-alanine, beta-homoserine, beta-homophenylalanine, beta-homolysine, beta-homotryptophan, 2-amino-3-benzo[1,3]dioxol-5-yl-propionic acid, 3-amino-3-(3-fluorophenyl)-propionic acid, 3-amino-3-(3,5-dichlorophenyl)-propionic acid, 3-amino-3-(3-pyridyl)-propionic acid, 3-amino-3-(3-pyridyl)-propionic acid, 3-amino-3-(3,4-dimethoxyphenyl)-propionic acid, 3-amino-3-(6-methoxy-pyridin-3-yl)-propionic acid, 3-amino-4-(3,4-difluorophenyl)-butyric acid, 3-amino-4-(4-fluorophenyl)-butyric acid, 3-amino-5-hexanoic acid, 2-tetrahydroisoquinoline-acetic acid, 3-amino-5-phenylpentanoic acid, and azetidine-3-carboxylic acid.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2$—NH—, —$CH_2$—$CH_2$—, —CH=CH— (cis and trans), —$COCH_2$—, —CH(OH)$CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p 267 (1983); Spatola, A. F., Vega Data (March 1983), Vol. 1. Issue 3, "Peptide Backbone Modifications" (general review); Morely, J. S., Trends Pharma Sci (1980) pp. 463-468 (general review); Hudson, D. et al., (1979) Int J Pept Prot Re 14: 177-185 (—$CH_2$—NH—, —$CH_2$—$CH_2$—); Spatola, A. F. et al., (1986) Life Sci 38:1243-1249 (—$CH_2$—S—); Hann, M. M., (1982) J Chem Soc Perkin Trans I 307-314 (—CH=CH—, cis and trans); Almquist, R. G. et al., (1980) J Med Chem 23: 1392 (—COCH$_2$—); Jennings-White, C et al., (1982) Tetrahedron Lett 23:2533 (—COCH$_2$—); Szelke, M et al., European Appln. EP 45665 (1982) CA: 97: 39405 (1982) (—CH(OH)CH$_2$—); Holladay, M. W. et al., (1983) Tetrahedron Lett 24:4401-4404 (—C(OH)CH$_2$—); and Hruby, V. J., (1982) Life Sci 31:189-199 (—CH$_2$—S—); each of which is incorporated herein by reference.

In another embodiment, a non-peptide linkage is —CH$_2$NH—. Such peptide mimetics may have significant advantages over peptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptide mimetics are possible. For example, cyclic peptides, in which the necessary conformation is stabilized by non-peptides, are specifically contemplated, U.S. Pat. No. 5,192,746 to Lobl, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred et al., J. Med. Chem. 37:3882 (1994), hereby incorporated by reference herein in its entirety) describe non-peptide antagonists that mimic the peptide sequence. Likewise, Ku et al., J. Med. Chem 38:9 (1995) (hereby incorporated by reference herein in its entirety) further elucidates the synthesis of a series of such compounds.

Further modifications following synthesis may be implemented. For example, the peptides may be further chemically modified, i.e. carbamylated, acetylated, succinylated, guanidated, nitrated, trinitrophenylated, amidinated, etc., in accordance with 20030072737-A1.

Additionally, the peptides may consist of recombinant peptides—muteins. The disclosed mutations may include substitutions, deletions, including internal deletions, additions, including additions yielding fusion proteins, or conservative substitutions of amino acid residues within and/or adjacent to the amino acid sequence, but that result in a "silent" change, and non-conservative amino acid changes and larger insertions and deletions.

As mentioned above, either conservative or non-conservative amino acid substitutions can be made at one or more amino acid residues. Both conservative and non-conservative substitutions can be made. Conservative replacements are those that take place within a family of amino acids that are related in their side chains. Genetically encoded amino acids can be divided into four families: (1) acidic=Asp (D), Glu (G); (2) basic=Lys (K), Arg (R), His (H); (3) nonpolar (hydrophobic)=Cys (C), Ala (A), Val (V), Leu (L), Ile (I), Pro (P), Phe (F), Met (M), Trp (W), Gly (G), Tyr (Y); and (4) uncharged polar=Asn (N), Gln (Q), Ser (S), Thr (T). Non-polar may be subdivided into: strongly hydrophobic=Ala (A), Val (V), Leu (L), Ile (I), Met (M), Phe (F); and moderately hydrophobic=Gly (G), Pro (P), Cys (C), Tyr (Y), Trp (W). In alternative fashion, the amino acid repertoire can be grouped as (1) acidic=Asp (D), Glu (G); (2) basic=Lys (K), Arg (R), His (H), (3) aliphatic=Gly (G), Ala (A), Val (V), Leu (L), Ile (I), Ser (S), Thr (T), with Ser (S) and Thr (T) optionally be grouped separately as aliphatic-hydroxyl; (4) aromatic=Phe (F), Tyr (Y), Trp (W); (5) amide=Asn (N), Gln (Q); and (6) sulfur-containing=Cys (C) and Met (M). (See, for example, Biochemistry, 4th ed., Ed. by L. Stryer, WH Freeman and Co., 1995, which is incorporated by reference herein in its entirety).

Alternatively, mutations can be introduced randomly along all or part of the coding sequence of a peptide, such as by saturation mutagenesis, and the resultant mutants can be screened for biological activity to identify mutants that retain activity. Following mutagenesis, the encoded peptide can be expressed recombinantly and the activity of the recombinant peptide can be determined.

In another embodiment, the peptide may be further modified through the additions of polymers (such as polyethylene glycol), sugars, or additional proteins (such as a fusion construct) in an effort to extend the half-life of the peptide or enhance the peptide's tissue protective effects. Examples of such modifications are disclosed within WO/04022577 A3 and WO/05025606 A1, which are incorporated herein by reference. For example, a polyethylene glycol polymer can be attached to GDKA (SEQ ID NO:3), GDKARYEREM (SEQ ID NO:1) or GDKARYEREA (SEQ ID NO:2) to form the pegylated analogues.

Depending on the conjugation chemistry selected and the number of reactive sites already present or created on the peptide, one, two, or a selected number of polymers can be appended in a reproducible manner. The principal mode of attachment of a PEG, and its derivatives, to peptides is a non-specific bonding through a peptide amino acid residue (see e.g., U.S. Pat. Nos. 4,088,538, 4,496,689, 4,414,147, 4,055,635, and PCT WO 87/00056). Another mode of attaching PEG to peptides is through the non-specific oxidation of glycosyl residues on a glycopeptide (see e.g., WO 94/05332). In these non-specific methods, PEG is added in a random, non-specific manner to reactive residues on a peptide backbone.

7. ASSAYS FOR TESTING PEPTIDES

Various assays can be used to determine the utility of the above noted peptides for use in the therapeutic methods provided herein. Assays for tissue protection are described in, for example, U.S. Pat. Nos. 6,531,121; 7,345,019; 7,410,941; 7,767,643; and 8,071,554. Additionally, one of ordinary skill in the art will recognize that the peptide's ability to prevent, mitigate or treat a disease or disorder associated with tissue damage or damage, associated with an effect, or a symptom of the disease or disorder may be confirmed through various assays both in vitro and in vivo, although in certain embodiments in vivo assays may be used.

7.1 Tissue Protective Assays and Models

The peptides utilized in the current method exhibit tissue protective properties, i.e. anti-apoptotic, neuritogenic, neuroprotective, etc. Peptides provided herein may be tested for tissue protective activity, e.g., protecting cells, tissues or organs. Protective activities may be further tested using in vitro and in vivo assays. In vitro tests that are indicative of tissue protective activity include, for example, cell proliferation assays, cell differentiation assays, or detecting the presence of proteins or nucleic acids upregulated by tissue protective receptor complex, e.g. tissue protective cytokine receptor complex, activity, e.g., nucleolin, neuroglobin, cytoglobin, or frataxin. Neuroglobin, for example, may be involved in facilitating the transport or the short-term storage of oxygen. Therefore, oxygen transport or storage assays may be used as an assay to identify or screen for compounds which modulate tissue protective activity.

Neuroglobin is expressed in cells and tissues of the central nervous system in response to hypoxia or ischemia and may provide protection from injury (Sun et al. 2001, PNAS 98:15306-15311; Schmid et al., 2003, J. Biol. Chem. 276: 1932-1935, each of which is incorporated by reference herein in its entirety). Cytoglobin may play a similar role in protection, but is expressed in a variety of tissues at varying levels (Pesce et al., 2002, *EMBO* 3:1146-1151, which is incorporated by reference herein in its entirety). In one embodiment, the levels of an upregulated protein in a cell may be measured before and after contacting the peptide to a cell. In certain embodiments, the presence of an upregulated protein associated with tissue protective activity in a cell, may be used to confirm the tissue protective activities of a peptide.

Nucleolin may protect cells from damage. It plays numerous roles in cells including modulation of transcription processes, sequence specific RNA-binding protein, cytokinesis, nucleogenesis, signal transduction, apoptosis induced by T-cells, chromatin remodelling, or replication. It can also function as a cell surface receptor DNA/RNA helicase, DNA-dependent ATPase, protein shuttle, transcription factor component, or transcriptional repressor (Srivastava and Pollard, 1999, *FASEB J.*, 13:1911-1922; and Ginisty et al., 1999, *J. Cell Sci.*, 112:761-772, each of which is incorporated by reference herein in its entirety).

Expression of an upregulated protein may be detected by detecting mRNA levels corresponding to the protein in a cell. The mRNA can be hybridized to a probe that specifically binds a nucleic acid encoding the upregulated protein. Hybridization may consist of, for example, Northern blot, Southern blot, array hybridization, affinity chromatography, or in situ hybridization.

Tissue protective activity of the peptides provided herein can also be detected using in vitro neuroprotection assays. For example, primary neuronal cultures may be prepared from new born rat hippocampi by trypsinization, and cultured as by any method known in the art and/or described herein e.g. in MEM-II growth medium (Invitrogen), 20 mM D-glucose, 2 mM L-glutamine, 10% Nu-serum (bovine; Becton Dickinson, Franklin Lakes, N.J.), 2% B27 supplement (Invitrogen), 26.2 mM $NaHCO_3$, 100 U/ml penicillin, and 1 mg/ml streptavidin (see, e.g., Leist et al., 2004, Science 305:239-242, hereby incorporated by reference in its entirety). One day after seeding, 1 µM cytosinearabinofuranoside is added. Thirteen day old cultures are then preincubated with increasing doses of the peptide of interest (3-3000 pM) for 24 h. On day 14, the medium is removed and the cultures challenged with 300 µM NMDA in PBS at room temperature (RT). After 5 min, pre-conditioned medium is returned to the cultures which are then returned to the incubator for 24 h. The cells are fixed in paraformaldehyde, stained by Hoechst 33342 (Molecular Probes, Eugene, Oreg.) and condensed apoptotic nuclei may be counted. NGF (50 ng/ml) and MK801 (1 µM) are included as positive controls.

Animal model systems can be used to demonstrate the tissue protective activity of a compound or to demonstrate the safety and efficacy of the compounds identified by the screening methods described herein. The compounds identified in the assays can then be tested for biological activity using animal models for a type of tissue damage, disease, condition, or syndrome of interest. These include animals engineered to contain the tissue protective receptor complex coupled to a functional readout system, such as a transgenic mouse.

Animal models that can be used to test the efficacy of the cell or tissue protective activity of an identified compound are known in the art and include, for example, protection against the onset of acute experimental allergic encephalomyelitis in Lewis rats, restoration or protection from diminished cognitive function in mice after receiving brain trauma, cerebral ischemia ("stroke") or seizures stimulated by excitotoxins (Brines et al., 2000, *PNAS*, 97:10295-10672, which is incorporated by reference herein in its entirety), protection from induced retinal ischemia (Rosenbaum et al., 1997, *Vis. Res.* 37:3443-51 which is incorporated by reference herein in its entirety), protection from injury to the sciatic nerve, and protection from ischemia-reperfusion injury to the heart (in vitro cardiomyocyte studies and in vivo ischemia-reperfusion injury, see, e.g., Calvillo et al., 2003, *PNAS* 100:4802-4806 and Fiordaliso et al., 2005, *PNAS* 102:2046-2051, each of which is hereby incorporated by reference in its entirety). Such assays are described in further detail in Grasso et al. (2004) *Med Sci Monit* 10: BR1-3, PCT publication no. WO02/053580, or PCT application PCT/US2006/031061 each of which is incorporated by reference herein in its entirety. Other assays for determining tissue protective activity of a peptide are well known to those of skill in the art.

Diabetes mouse or rate model in which the diabetes is induced by streptozotocin (STZ) is available and well-known to a person skilled in the art. STZ is a glucosamine-nitrosourea compound derived from *Streptomyces achromogenes* that is used clinically as a chemotherapeutic agent in the treatment of pancreatic β cell carcinoma. STZ damages pancreatic β cells, resulting in hypoinsulinemia and hyperglycemia. At high doses, typically given singly, STZ targets 0 cells by its alkylating property similar to that of cytotoxic nitrosourea compounds. At low doses, generally given in multiple exposures, STZ elicits an immune and inflammatory reaction, presumably related with the release of glutamic acid decarboxylase autoantigens. In the the low dose STZ-induction, the destruction of β cells and induction of the hyperglycemic state is a result of inflammatory infiltrates including lymphocytes in the pancreatic islets. The STZ-induced diabetes mouse or rat model has been described by Graham et al. (Graham et al. 2011 *Comp Med.* 61: 356-360) and Lenzen S. (Lenzen S. 2008 *Diabetologia* 51:216-226).

As demonstrated by Beiswenger et al., an increase in thermal withdrawal latency correlates with the loss of epidermal innervation, which is shown as a reduction in the density of intra-epidermal nerve fibers, four weeks after the initiation of STZ-induced diabetis in mice (Beiswenger et al., 2008 *Neurosci Lett.* 442:267). Smith et al. also reported that loss of intra-epidermal nerve fibers is a valid surrogate measure of neuropathy severity and progression (Smith et al., 2006 *Diabetes Care* 29:1294). Therefore, the tissue protective effects of a peptide on thermal withdrawal latency in STZ-induced diabetic mouse can be tested to demonstrate its ability to protect from nerve damage in diabetic neuropathy.

To test a peptide in a diabetic neuropathy mouse model, male Swiss Webster mice are given a single injection of STZ (180 mg/kg i.p.) to induce insulin-deficient diabetes. Hyperglycemia is confirmed 3 days thereafter, and to ensure induction of sufficient neuropathy, only mice with blood glucose levels exceeding 15 mmol/l are used. After four weeks of untreated diabetes, tissue protective peptides or control treatment (phosphate buffered saline (PBS)) is administered as eye drops (50 microliters of 50 nanomolar solution to both eyes for five days/week. The peptide of SEQ ID NO: 282 from U.S. Pat. No. 8,853,358 is used as the positive control. After 12 weeks of therapy, mice are tested for paw thermal sensitivity. To measure thermal withdrawal latency, mice are placed in enclosures with a warmed glass floor and a mobile radiant heat source is directed at the plantar surface of one hind paw. The heat is increased 0.9° C. per second to ensure the paw withdrawal response involved activation of heat-sensitive C-fibers (Yeomans et al., 1996 *Pain* 68:133). The time from initiation of heating to paw withdrawal is recorded in 4 separate trials 5 minutes apart, with the median value of the last 3 trials used for each mouse. The paw withdrawal time is plotted and compared between the peptide-treated group and the control group.

Similarly, an animal model of neuropathic pain can be used to test the efficacy of the tissue protective peptides. The rats used in this study are eight-week-old female Sprague-Dawley rats (Charles River, Maastricht, The Netherlands). Animals are anesthetized with 6% sevoflurane induction and 3% maintenance. A small incision is made in the lateral surface of the left hind limb of the animal, exposing the muscles. The trifurcation of the sciatic nerve is revealed by blunt preparation between the two heads of the biceps femoris muscle. Next, the tibial and common peroneal nerves are tightly ligated with 5-0 silk in rats and 6-0 silk in mice and cut to remove 2-4 mm of the distal nerve. The sural nerve is left intact. In order to prevent spontaneous nerve reconnection, the transected nerves are displaced. During the surgical procedure, great care is taken not to stretch or touch the sciatic or sural nerves. The wound is closed in two layers with 4-0 silk in rats and 6-0 silk in mice and a single dose of 0.01 and 0.05 mg/kg buprenorphine is administered in rats and mice, respectively, to relieve postoperative pain. After exposure spared nerve injury (SNI) is induced and the wound is closed in two layers with 4-0 (rats) or 6-0 (mice) silk and a single dose of 0.01 (rats) mg/kg buprenorphine is administered to relief postoperative pain. During the surgical procedure, great care is taken not to stretch or touch the exposed nerves.

Treatment is initiated at 24-h after induction of the SNI, which includes intraperitoneal injections of tissue protective peptides or control at 2 day intervals. The peptide of SEQ ID NO: 282 from U.S. Pat. No. 8,853,358 is used as the positive control. Tactile allodynia is tested with the use of different von Frey hairs (Semmes-Weinstein Monofilaments, North Coast Medical Inc., San Jose, Calif.) with increasing stiffness (0.004-15 g) causing incremental forces to be exerted on the plantar surface of the affected hind paw. The hairs are applied 10 times at intervals of 1-2 s to slightly different loci within the test area. The force necessary to evoke a pain reflex by a brisk paw withdrawal is recorded and no further filaments are applied to the paw that showed a response. The recorded force is compared among the peptide-treated groups and the control groups.

Similarly, a competitive assay can be utilized to determine if a peptide is tissue protective.

In a 96 well plate eight 1:2 serial dilutions of a known tissue protective compound/biomarker in suitable growth medium, and the same dilution series of the known tissue protective compound/biomarker and an excess of the peptide of interest are plated. The final volume of each dilution should be about 100 µl. Once again, the BaF3 cells are seeded into the plates as disclosed supra and allowed to incubate. After an appropriate amount of time, the cells are washed and the plate is read on a fluorescent plate reader or by any other suitable method known in the art to detect the biomarker. If the readout of the plates and/or wells containing the known tissue protective compound/biomarker and peptide of interest is less than the readout of the plates containing only the known tissue protective compound/biomarker then the peptide of interest is tissue protective.

Many protein factors discovered to date, including all known cytokines, have exhibited activity in one or more factor-dependent cell proliferation assays, and hence these assays serve as a convenient confirmation of cytokine activity. The activity of a peptide can be evidenced by any one of a number of routine factor dependent cell proliferation assays for cell lines including, without limitation, 32D, DA2, DA1G, T10, B9, B9/11, BaF3, MC9/G, M+(preB M+), 2E8, RBS, DA1, 123, T1165, HT2, CTLL2, TF-1, Mole and CMK. These cells are cultured in the presence or absence of a peptide, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, 1983, J. Immunol. Meth. 65:55-63, which is incorporated by reference herein in its entirety).

Additionally, measuring the activation of a cellular signaling pathway by measuring one or more phosphorylation intermediates is also well known to one of ordinary skill in the art. For example, the activity of a peptide described herein can be measured by assaying the activation of Jak2, which is essential for signaling through a variety of cytokine receptors (Parganas, et al., 1998, Cell 93:385-395) or measuring the activation of AKT by phosphorylation using a method well known in the art (Liu, et al., 2014, Nature 508:541-545) and/or the method described in Example 2. One of skill in the art would recognize that activation of such a signaling pathway is an indirect method of assaying the tissue protective activity of a peptide described herein. Measuring activation of a signaling pathway (e.g., phosphorylation) when combined with one or more additional tissue protective assays described herein can further provide evidence of tissue protective activity of a peptide described herein.

In one assay for the activation of AKT by phosphorylation, HUVECs are purchased from Cell Applications (San Diego, Calif.) and grown in medium EGM-2 supplemented with 2% fetal calf serum (FCS) and penicillin/streptomycin (P/S) at 37° C. under air containing 5% CO2 in a humidified incubator. Preliminary experiments can be performed to determine the time course of the phosphorylation of Akt following stimulation by compounds that activated the tissue protective receptor. In some assays, the phosphorylation of Akt reaches a maximum 10 minutes following stimulation by compounds that activated the tissue protective receptor. After HUVECs are treated with tissue protective peptides or controls, cell lysates are prepared and Western blot is performed using anti-Akt and anti-phospho-Akt antibodies (Cell Signaling Technology, Danvers, Mass.). To perform the Western blot, cell lysates are subjected to SDS-PAGE, and transferred to nitrocellulose membranes (Amersham Biosciences, Piscataway, N.J.). The membrane is blocked for 1 h at room temperature with PBS containing 2% BSA and 0.05% Tween 20. The blots are incubated overnight at 4° C. or for 4 h at room temperature with a primary antibody against phospho-Akt, followed by incubation for 1 h with a secondary, horseradish peroxidase-conjugated antibody. Then the blots are reprobed with an antibody against Akt to confirm equal protein loading. Immuno-reactive bands are visualized using ECL (Amersham Biosciences, Piscataway, N.J.). In some assays, the intensities of phosphorylated Akt bands are compared between the control cells and the peptide-treated cells. In some assays, the ratios of the intensity of the phosphor-Akt band to that of the total Akt band are compared the control cells and the peptide-treated cells.

If a peptide exhibits a tissue protective activity, one of ordinary skill in the art would recognize that it would be beneficial to verify the result using one of the neuroprotective and tissue protective assays known to those skilled in the art, such as, but not limited to, P-19 and PC-12 cell assays. Additionally, various in vivo models such as animal models related to spinal cord injury, ischemic stroke, peripheral nerve damage, wounds, or damage to the heart, eyes, kidneys, etc. would be helpful in further characterizing the peptide.

7.2 Assays for Specific Indications

Toxic Agents

The isolated peptides to be used within the method provided herein may be demonstrated to inhibit damage, effects or symptoms resulting from exposure to a toxic agent in vitro or in vivo using a variety of assays known in the art, or described herein.

Further peptides used within the method provided herein may be tested in various in vitro assays in the art to determine their ability to prevent, treat, ameliorate, or manage damage, effects or symptoms resulting from exposure to a toxic agent. In general, this is accomplished by selecting an appropriate cell line, subjecting that cell to a toxic agent of interest and treating a portion of the cells with a peptide of interest and determining the cells survival or response in the presence of the toxic agent and in the presence of the toxic agent and the peptide of interest. If the cell exhibits improved survival or a reduction of damage, effects or symptoms in the presence of the peptide, the peptide can be considered to be a possible therapeutic for toxic exposure. Further one of ordinary skill in the art will recognize that the peptides ability as a protectant can be evaluated by treating the cells with the peptide prior to the toxic agent challenge.

For example, suitable assays for toxic agents include, but are not limited to: Chemical Agents: a) skin cell lines such as J-774 (mouse macrophage derived cell line), CHO-K1 (strain of epithelial cell line derived from Chinese hamster ovary cells), and HeLa (human cervical carcinoma) (Sawyer, T. et al., Hypothermia as an adjunct to vesicant-induced skin injury, *Eplasty* 2008; 8:e25); b) corneal cell lines for vesicant agents (Amir, A. et al., The corneal epithelium in sulfur mustard ocular injury—In vitro and ex vivo studies, Proceedings of the U.S. Army Medical Defense Bioscience Review, Aberdeen Proving Ground, MD (2004)); c) macrophages (Amir A., et al., Sulfur mustard toxicity in macrophages: effect of dexamethasone, *J Appl Toxicol,* 20 Suppl 1:S51-8 (2000)); d) upper respiratory tract cell lines (Andrew, D. J. and C. D. Lindsay, Protection of human upper respiratory tract cell lines against sulphur mustard toxicity by gluthione esters, *Hum Exp Toxicol* 17(7):387-95 (1998); Calvet et al., Airway epithelial damage and release of inflammatory mediators in human lung parenchyma after sulfur mustard exposure, *Hum Exp Toxicol* 18(2):77-81 (1999); Langford, A. M. et al., The effect of sulphur mustard on glutathione levels in rat lung slices and the influence of treatment with arylthiols and cysteine esters, *Hum Exp Toxicol* 15(8):619-24); e) skin models (Blaha et al., Effects of CEES on inflammatory mediators, heat shock protein 70A, histology and ultrastructure in two skin models, *J Appl Toxicol* 20 Suppl 1:S101-8 (2000); Henemyre-Harris et al., An in vitro wound healing model to screen pharmacological interventions for the effective treatment of cutaneous sulfur mustard injuries, Proceedings of the U.S. Army Medical Defense Bioscience Review, Aberdeen Proving Ground, MD (2004))(See generally, www.counteract.rutgers.edu/in-vitro.html for additional literature on appropriate in vitro studies); Radiation Agents: a) endothelial cells (Abderrahmani, R. et al., Role of plasminogen activator inhibitor type-1 in radiation-induced endothelial cell apoptosis, *Radioprotection* 2008, vol 43, no. 5, b) neuroimmune cells (afferent nerves, enteric sensory nerves, mast cells) (Wang, J. et al., Neuroimmune interactions: potential target for mitigating or treating intestinal radiation injury, *British Journal of Radiology* (2007) 80, S41-S48), c) blood or lymphocyte cultures (Lloyd D C et al., *Phys Med Biol* 18(3):421-31 (1973); Lloyd D C et al., *Mutat. Res.* 179(2): 197-208 (1987); Blakely W F et al., *Stem Cells* 13 (Suppl 1):223-30 (1995); Gotoh E et al., *Int. J. Radiation. Biol.* 81(1):33-40 (2005)); Biological Agents: (a) peripheral blood mononuclear cells (Rasha, H. et al. Modeling of SEB-induced host gene expression to correlate in vitro to in vivo responses: Microarrays for biodefense and environmental applications, *Biosensors and Bioelectrics* (2004) vol. 20, no. 4, 719-727).

Further, suitable in vivo assays are known in the art for evaluating the effect of therapeutics on toxic agent exposure. Animal models using rats, mice, guinea pigs, rabbits, pigs, sheep, ferrets, dogs and non-human primates are contemplated as well as transgenic animals that are particularly susceptible to a toxic agent (CD46 mice). In particular, assays known in the art include, but are not limited to: Chemical Agents: (1) Reid, F. M., Sulfur mustard induced skin burns in weanling swine evaluated clinically and histopathologically, *Journal of applied toxicology*, vol. 20 (51), pages S153-S160 (2001); (2) Isidore, M. A. et al., A dorsal model for cutaneous vesicant injury 2-chloroethyl ethyl sulfide using c57bl/6 mice, *Cutaneous and ocular toxicology*, Vol. 26 (3), 265-276 (2007); (3) See generally, www.counteract.rutgers.edu/animal.html; (4) Kassa J., et al., The Choice: HI-6, pradoxime or Obidoxime against Nerve Agents?, www.asanite.com/ASANews-97/Antidot-Choice.html, (5) Shih, T M et al., Organophosphorus nerve agents-induced seizures and efficacy of atropine sulfate as anticonvulsant treatment, *Pharmacol-Biochem-Behav.* 1999 September, 64(1), 147-53, (6) Luo, C et al., Comparison of oxime reactivation and aging of the nerve agent-inhibited monkey and human acetylcholinesterases, *Chemico-Biological Interactions,* 175(1-3), 261-266 (2008); Radiation Agents: (1) W. F. Blakely et al., In Vitro and Animal Models of Partial-Body Dose Exposure: Use of Cytogenic and Molecular Biomarkers for Assesment of Inhomogeneous Dose Exposures and Radiation Injury, PB-Rad-Injury 2008 Workshop, May 5-6, 2008 AFRRI, Bethesda, Md.; (2) Augustine, A et al., Meeting Report: Animal Models of Radiation Injury, Protection and Therapy, *Radiation Research* 164: 100-109 (2005); (3) Houchen, C et al. Pro-survival and antiapoptotic effects of $PGE_2$ in radiation injury are mediated by $EP_2$ receptor in intestine, *Am J Physiol Gastrointest Liver Physiol,* 284: G490-G498, 2003; (4) Jichun Chen, Animal Models for Acquired Bone Marrow Failure Syndromes, *Clinical Medicine & Research* 3(2): 102-108: Biological Agents: (1) Biodefense: Research Methodology and Animal Models, James R. Swearengen (editor) 2006 CRC Press.

Inflammation

Additionally, various in vitro models of inflammation may be used to evaluate a peptides ability to protect or treat the damage, symptoms, or effects of inflammation on the body. Initially, the ability of the peptide to modulate an inflammatory mediator can be confirmed by measuring the levels of the inflammatory mediator in an inflammatory assay after treatment with the peptide by known methods, including but not limited to, ELISA, cytometric bead array analysis, high-sensitivity and immunonephelometric assays. For example to determine if the peptide modulates either TNF-α or IL-1, a murine model of LPS-mediated cytokine production would be performed. Some mice in the murine model would be pretreated with the peptide of interest and then challenged with LPS while others would be saline treated. Blood would then be collected and the TNF-α and IL-1 levels in the blood could be determined by an ELISA kit (OPT-EIA mouse TNF-α and IL-1 ELISA kits (BD Biosciences). If the TNF-α levels in the treated animals are lower than the TNF-α levels in the saline treated animals then the peptide could be considered to modulate TNF-α. In some embodiments, the peptide would be tested for its ability to modulate more than one inflammatory mediator, and in one embodiment, it would be a mediator other than or in addition to TNF-α, and in one embodiment, it would be histamine. Similarly, the peptides may be tested in additional in vitro assays including, but not limited to, those disclosed in Lopata, Andreas L., Specialized in vitro Diagnostic Methods In The Evaluation Of Hypersensitivity—An Overview, *Current Allergy & Clinical Immunology*, March 2006, Vol. 19, No. 1, (histamine and tryptase assays), and Arulmozhi et al., Pharmacological Investigations of *Sapindus trifoliatus* in various in vitro and in vivo models of inflammation, *Indian Journal of Pharmacology*, vol. 37:2, 96-102 (2005) (5-lipoxygenase (5-LO), cyclo-oxygenase (COX), leukotrine B4 (LTB4) and nitric oxide synthase (NOS)).

Further, in vivo assays of inflammation may be useful in evaluating the peptides utility as a therapeutic against toxic agents. In vivo assays, including, but not limited to, murine EAE models, those utilizing transgenic mice such as MDBiosciences DSS IBD murine model of severe colitis, the MDBioscience TNBS IBD murine model of inflammatory bowel disease, models involving IL-1 knockout mice disclosed within U.S. Pat. No. 6,437,216, or models of transgenic mice involving TNF-α as disclosed within Probert et al. Spontaneous inflammatory demyelinating disease in transgenic mice showing CNS-specific expression of tumor necrosis factor α. *Proc. Natl. Acad. Sci.* 1995 USA 92, 11294-11298, Kontoyiannis et al. Impaired on/off regulation of TNF biosynthesis in mice lacking TNF AU-rich elements: implications for joint and gut-associated immunopathologies. *Immunity* 10:387-398, 1999, Keffer et al. Transgenic mice expressing human tumour necrosis factor: a predictive genetic model of arthritis. *EMBO J.* 1991 December; 10(13): 4025-31, or models using chemical or synthetic challenges to induce the inflammation such as models of asthma and chronic obstructive pulmonary disease disclosed in WET 307:373-385, 2003, adjuvant arthritis models as disclosed in EP 1 777 234; murine LPS shock models, murine LPS lung models, acute paw inflammation models, or histamine challenge wheal formation model as as described in Brines M. & Cerami A. 2012, Molecular Medicine 18:486-496.

Further, the efficacy of the compounds in humans using well-known clinical studies such as the skin prick test and bronchoprovocation test disclosed in Ravensberg et al. "Validated safety predictions of airway responses to house dust mites in asthma," *Clinical and Experimental Allergy*, 37:100-107 (2007); asthma studies as disclosed in Diamant et al. "Methods used in clinical development of novel anti-asthma therapies," *Respiratory Medicine* (2008) 102, 332-338, or nasal allergen challenge as disclosed in Boot et al. "Nasal Nitric Oxide: longitudinal reproducibility and the effects of a nasal allergen challenge in patients with allergic rhinitis," *Allergy* 2007:62:378-384.

Cancer

The isolated peptides to be used within the method provided herein may be demonstrated to inhibit tumor cell proliferation, cell transformation and tumorigenesis in vitro or in vivo using a variety of assays known in the art, or described herein. Such assays can use cells of a cancer cell line or cells from a patient. Many assays well-known in the art can be used to assess such survival and/or growth; for example, cell proliferation can be assayed by measuring $^3$H-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3 or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz, Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

Provided herein are cell cycle and cell proliferation analyses by a variety of techniques known in the art, including but not limited to the following:

As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, *Int. J. Cancer* 38, 369; Campana et al., 1988, *J. Immunol. Meth.* 107, 79).

Cell proliferation may also be examined using ($^3$H)-thymidine incorporation (see e.g., Chen, J., 1996, *Oncogene* 13:1395 403; Jeoung, J., 1995, *J. Biol. Chem.* 270:18367 73). This assay allows for quantitative characterization of S-phase DNA synthesis. In this assay, cells synthesizing DNA will incorporate $^3$H-thymidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, *Curr. Biol.* 6:189 199; Vassilev et al., 1995, *J. Cell Sci.* 108:1205 15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In one embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidum iodide assay (see e.g., Turner, T., et al., 1998, *Prostate* 34:175 81). Alternatively, the DNA ploidy may be determined by quantitation of DNA Feulgen staining (which binds to DNA in a stoichiometric manner) on a computerized microdensitometry staining system (see e.g., Bacus, S., 1989, *Am. J. Pathol.* 135:783 92). In another embodiment, DNA content may be analyzed by preparation of a chromosomal spread (Zabalou, S., 1994, *Hereditas.* 120:127 40; Pardue, 1994, Meth. Cell Biol. 44:333 351).

The expression of cell-cycle proteins (e.g., CycA, CycB, CycE, CycD, cdc2, Cdk4/6, Rb, p21 or p27) provide crucial information relating to the proliferative state of a cell or population of cells. For example, identification in an antiproliferation signaling pathway may be indicated by the induction of p21cip1. Increased levels of p21 expression in cells results in delayed entry into G1 of the cell cycle (Harper et al., 1993, *Cell* 75:805 816; Li et al., 1996, *Curr. Biol.* 6:189 199). p21 induction may be identified by immunostaining using a specific anti-p21 antibody available commercially (e.g., from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a peptide provided herein. In one embodiment the length of the cell cycle is determined by the doubling time of a population of cells (e.g., using cells contacted or not contacted with one or more peptide provided herein). In another embodiment, FACS analysis is used to analyze the phase of cell cycle progression, or purify G1, S, and G2/M fractions (see e.g., Delia, D. et al., 1997, *Oncogene* 14:2137 47).

Lapse of cell cycle checkpoint(s), and/or induction of cell cycle checkpoint(s), may be examined by the methods described herein, or by any method known in the art. Without limitation, a cell cycle checkpoint is a mechanism which ensures that certain cellular events occur in a particular order. Checkpoint genes are defined by mutations that allow late events to occur without prior completion of an early event (Weinert, T., and Hartwell, L., 1993, *Genetics*, 134:63 80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. Provided herein are assays involved detected post-translational modifications (e.g., phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase HPLC (see e.g., Glover, C., 1988, *Biochem. J.* 250:485 91; Paige, L., 1988, *Biochem J.;* 250:485 91).

Activity of signaling and cell cycle proteins and/or protein complexes is often mediated by a kinase activity. Also provided is analysis of kinase activity by assays such as the histone H1 assay (see e.g., Delia, D. et al., 1997, *Oncogene* 14:213747).

The peptides used within the method provided herein can also be demonstrated to alter cell proliferation in cultured cells in vitro using methods which are well known in the art. Specific examples of cell culture models include, but are not limited to, for lung cancer, primary rat lung tumor cells (Swafford et al., 1997, *Mol. Cell. Biol.,* 17:1366 1374) and large-cell undifferentiated cancer cell lines (Mabry et al., 1991, *Cancer Cells,* 3:53 58); colorectal cell lines for colon cancer (Park and Gazdar, 1996, *J. Cell Biochem.* Suppl. 24:131 141); multiple established cell lines for breast cancer (Hambly et al., 1997, *Breast Cancer Res. Treat.* 43:247 258; Gierthy et al., 1997, *Chemosphere* 34:1495 1505; Prasad and Church, 1997, *Biochem. Biophys. Res. Commun.* 232:14 19); a number of well-characterized cell models for prostate cancer (Webber et al., 1996, *Prostate,* Part 1, 29:386 394; Part 2, 30:58 64; and Part 3, 30:136 142; Boulikas, 1997, *Anticancer Res.* 17:1471 1505); for genitourinary cancers, continuous human bladder cancer cell lines (Ribeiro et al., 1997, *Int. J. Radiat. Biol.* 72:11 20); organ cultures of transitional cell carcinomas (Booth et al., 1997, *Lab Invest.* 76:843 857) and rat progression models (Vet et al., 1997, *Biochim. Biophys Acta* 1360:39 44); and established cell lines for leukemias and lymphomas (Drexler, 1994, *Leuk. Res.* 18:919 927, Tohyama, 1997, *Int. J. Hematol.* 65:309 317).

The peptides provided herein can also be demonstrated to inhibit cell transformation (or progression to malignant phenotype) in vitro. In this embodiment, cells with a transformed cell phenotype are contacted with one or more peptides provided herein, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General Virology, 3d Ed., John Wiley & Sons, New York, pp. 436446).

Loss of invasiveness or decreased adhesion may also be used to demonstrate the anti-cancer effects of the peptides used in the method provided herein. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell—cell adhesion. Such E-cadherin-mediated adhesion can result in phenotypic reversion and loss of invasiveness (Hordijk et al., 1997, *Science* 278:1464 66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, *Science* 278:1464 66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, *Biochem. Biophys. Res. Commun.* 193:518 25).

The peptides used in the method provided herein can also be demonstrated to inhibit tumor formation in vivo. A vast number of animal models of hyperproliferative disorders, including tumorigenesis and metastatic spread, are known in the art (see Table 317-1, Chapter 317, "Principles of Neoplasia," in Harrison's Principles of Internal Medicine, 13th Edition, Isselbacher et al., eds., McGraw-Hill, N.Y., p. 1814, and Lovejoy et al., 1997, *J. Pathol.* 181:130 135). Specific examples include for lung cancer, transplantation of tumor nodules into rats (Wang et al., 1997, *Ann. Thorac. Surg.* 64:216 219) or establishment of lung cancer metastases in SCID mice depleted of NK cells (Yono and Sone, 1997, *Gan To Kagaku Ryoho* 24:489 494); for colon cancer, colon cancer transplantation of human colon cancer cells into nude mice (Gutman and Fidler, 1995, *World J. Surg.* 19:226 234), the cotton top tamarin model of human ulcerative colitis (Warren, 1996, *Aliment. Pharmacol. Ther.* 10 Supp 12:45 47) and mouse models with mutations of the adenomatous polyposis tumor suppressor (Polakis, 1997, *Biochim. Biophys. Acta* 1332:F127 F147); for breast cancer, transgenic models of breast cancer (Dankort and Muller, 1996, *Cancer Treat. Res.* 83:71 88; Amundadittir et al., 1996, *Breast Cancer Res. Treat.* 39:119 135) and chemical induction of tumors in rats (Russo and Russo, 1996, *Breast Cancer Res. Treat.* 39:7-20); for prostate cancer, chemically-induced and transgenic rodent models, and human xenograft models (Royai et al., 1996, *Semin. Oncol.* 23:35 40); for genitourinary cancers, induced bladder neoplasm in rats and mice (Oyasu, 1995, *Food Chem. Toxicol* 33:747 755) and xenografts of human transitional cell carcinomas into nude rats (Jarrett et al., 1995, 1 Endourol. 9:1 7); and for hematopoietic cancers, transplanted allogeneic marrow in animals (Appelbaum, 1997, *Leukemia* 11 (Suppl. 4):S15 S17). Further, general animal models applicable to many types of cancer have been described, including, but not restricted to, the p53-deficient mouse model (Donehower, 1996, *Semin. Cancer Biol.* 7:269 278), the Min mouse (Shoemaker et al., 1997, *Biochem. Biophys. Acta*, 1332:F25 F48), and immune responses to tumors in rat (Frey, 1997, *Methods*, 12:173 188).

For example, a peptide to be used in the method provided herein can be administered to a test animal, in one embodiment a test animal predisposed to develop a type of tumor, and the test animal subsequently examined for a decreased incidence of tumor formation in comparison with an animal not administered the peptide provided herein. Alternatively, a peptide provided herein can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the peptide provided herein.

In certain embodiments, an assay in which a cell line (e.g., a mouse macrophage cell line such as mJ774) is stimulated by lipopolysaccharide to secrete TNFα can be used to test the activity of a peptide described herein. This assay is decribed in detail in Bohr et al. 2015, Journal of Molecular Medicine 93(2):199-210.

8. THERAPEUTIC USE

8.1 Modulation of Mediators of the Body's Response

One of ordinary skill in the art would recognize that the peptides provided herein may be used to modulate the body's response to a disease or disorder associated with tissue damage. In particular, one example of mediators the peptides noted above may be used to modulate are inflammatory modulators, including but not limited to, plasma derived inflammatory mediators, such as bradykinins, C3, C5a, Factor XII, membrane attack complex, Hageman factor, plasmin, thrombin, lymphokines (macrophage activating factor (MAF), macrophage migration inhibition factor (MMIF), macrophage chemotactic factor (MCF), leukocyte migration inhibition factor (LMIF), histamine releasing factors (HRFs), and transfer factor (TF)); interleukins (IL-1, IL-2, IL-3, IL-4, ... IL-15); Tumor necrosis factors (TNF-α (cachectin), TNF-β (lymphotoxin)); Interferons (IFN-α, IFN-β, IFN-γ, IFN-w, IFN-τ); Colony stimulating factors (granulocyte colony stimulating factor (G-CSF), granulocyte-macrophage colony stimulating factor (GM-CSF), macrophage colony stimulating factor (M-CSF), and multi colony stimulating factor (IL-3)); polypeptide growth factors (acidic fibroblast growth factor (aFGF), basic fibroblast growth factor (bFGF), epidermal growth factor (EGF); nerve growth factor (NGF), platelet-derived growth factor (PDGF), and vascular endothelial growth factor (VEGF)); Transforming growth factors (TGF-α and TGF-β), α-Chemokines (IL-8, neutrophil-activating protein 2 (NAP-2), platelet factor-4 (PF-4), and β-thromboglobulin (βTG)); β-Chemokines (monocyte chemoattractant protein 1 (MCP-1), MCP-3, MIP-1α, macrophage inflammatory protein 1β (MIP-1β), regulated upon activation normal T expressed and presumably secreted chemokine (RANTES)) and Stress proteins (heat shock proteins (HSPs), glucose related proteins (GSPs), ubiquitin, and superoxide dismutase (Mn)), leukemia inhibitory factor (LIF), oncostatin (OSM), ciliary neurotrophic factor (CNTF), platelet basic protein (PBP), lysosome granules, histamine, serotonin, leukotriene B4, nitric oxide, and/or prostaglandins. In some embodiments, the peptides inhibit or suppress the activity of the mediators and in some embodiments, the peptides inhibit the activity of TNF-α, histamine, nitric oxide, and interleukins. In some embodiments, the peptides inhibit the activity of two or more inflammatory mediators.

8.2 Treatment or Prevention of Various Diseases, Disorders, and Conditions

The tissue protective peptides and peptide analogs provided herein are also useful as therapeutics for treatment or prevention of various diseases, disorders, and conditions. One skilled in the art would also recognize that such peptides and peptide analogs can be used to achieve modulation of a tissue protective receptor complex, e.g., tissue protective cytokine complex. Both in vitro and in vivo techniques that can be used for assessing the therapeutic indications of, for example, the compounds identified by the inventive assays disclosed above are disclosed in PCT Application No. PCT/US01/49479, U.S. patent application Ser. Nos. 10/188,905 and 10/185,841.

The aforementioned tissue protective peptides and peptide analogs provided herein may be useful generally for the prevention, therapeutic treatment, or prophylactic treatment of human diseases or disorders of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, connective tissue diseases, gastrointestinal diseases, endocrine and metabolic abnormalities, and aging. Examples of use include, but are not limited to, protection against and repair of injury resulting from trauma and resulting inflammation to the brain (ischemic stroke, blunt trauma, subarachnoid hemorrhage), spinal cord (ischemia, blunt force trauma, lesions), peripheral nerves (sciatic nerve injury, diabetic neuropathy, carpal tunnel syndrome), retinal (macular edema, diabetic macular edema, diabetic retinopathy, glaucoma), and heart (myocardial infarct, chronic heart failure, progressive heart failure). In particular, such diseases, disorders, and conditions include hypoxic conditions, which adversely affect responsive tissues, such as excitable tissues including, but not limited to, those noted above in Section 4.2 (xii), or those responsive cells tissues or organs. Therefore, the tissue protective peptides and peptide analogs provided herein can be used to treat or prevent damage to responsive tissue resulting from hypoxic conditions in a variety of conditions and circumstances. Non-limiting examples of such conditions and circumstances are provided in the table herein below.

The tissue protective peptides and peptide analogs are also of interest in the modulation of stem cell activity, stimulating the migration to regions of injury and aiding the repair process, e.g. in a regenerative role.

In the example of the protection of neuronal tissue pathologies treatable and preventable using tissue protective peptides and peptide analogs provided herein, such pathologies include those which result from reduced oxygenation of neuronal tissues. Any condition which reduces the availability of oxygen to neuronal tissue, resulting in stress, damage, and finally, neuronal cell death, can be treated using tissue protective peptides and peptide analogs provided herein. Generally referred to as hypoxia and/or ischemia, these conditions arise from or include, but are not limited to, stroke, stroke (ischemia/perfusion), stroke (middle cerebral artery), vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, inhalation emphysema, adult respiratory distress syndrome, hypotensive shock, septic shock, anaphylactic shock, insulin shock, sickle cell crisis, critical limb ischemia, cardiac arrest, dysrhythmia, nitrogen narcosis, hypoxemic hypoxia (altitude sickness, high altitude pulmonary edema, high altitude cerebral edema, sleep apnea, hypopnea, respiratory arrest, shunts), methaemoglobinaemia, histotoxic hypoxia, intrauterine hypoxia, and neurological deficits caused by heart-lung bypass procedures.

In one embodiment, for example, the tissue protective peptides and peptide analogs provided herein identified using the above-noted assays could be administered alone or as part of a composition to prevent injury or tissue damage resulting from risk of injury or tissue damage prior to, during, or subsequent to a surgical procedure or a medical procedure. For example, surgical procedures may include tumor resection or aneurysm repair and medical procedures may include labor or delivery. Other pathologies caused by or resulting from hypoglycemia which are treatable using tissue protective peptides and peptide analogs provided herein include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include, but are not limited to, diseases such as stroke, multiple sclerosis, hypotension, cardiac arrest, chronic heart failure, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The specific tissue protective peptides and peptide analogs provided herein may be used to treat or prevent inflammation resulting from disease conditions or various traumas, such as physically or chemically induced inflammation. The tissue protective peptides and peptide analogs are also contemplated for the treatment and prevention of inflammatory conditions in one or more organs or tissues including, but not limited to, the brain, spinal cord, connective tissue, heart, lung, kidney and urinary tract, pancreas, eyes and prostate. Non-limiting examples of such trauma include, but are not limited to those listed in Section 4.2 (xv). Further the tissue protective peptides may be used to treat or prevent inflammation resulting from ischemic and non-ischemic conditions including, but not limited to, allergies, allergic diseases, allergic symptoms, rheumatic diseases, sports related injuries, exposure to toxic agents, infections including viral, fungal, and bacterial, further examples of such conditions are disclosed above in Section 4.2 (iv), (v) and (xv). The inflammation may be acute or chronic. Further applications in the field of inflammation are noted within PCT/US2004/031789 filed Sep. 29, 2004 and published as WO 2005/032467.

The specific tissue protective peptides and peptide analogs provided herein may be used to treat central nervous and peripheral nervous system diseases resulting from demyelination or impairment of the myelin sheath. These diseases are defined as mainly involving inflammatory myelin sheath lesions of unknown origin, with the exception of myelination deficiency diseases, such as leukodystrophy, and diseases due to obvious causes. Multiple sclerosis (MS) is a typical disease among demyelinating diseases, and pathologically, it is characterized by changes, mainly, inflammatory demyelination, and gliosis. Since its etiology is unknown, its diagnosis is made based on its clinical features, i.e., spatial multiplicity and multiplicity over time of central nervous system lesions. Furthermore, acute disseminated encephalomyelitis (ADEM), inflammatory diffuse sclerosis, acute and subacute necrotizing hemorrhagic encephalomyelitis, and transverse myelitis are included in demyelinating diseases. Also, peripheral nervous tissues rely upon Schwann cells to maintain the myelin sheath, if these cells are impaired, peripheral demyelinating disease is caused.

The tissue protective peptides and peptide analogs provided herein may be used to treat or prevent conditions of, and damage to the heart including any chronic or acute pathological event involving the heart and/or associated tissue (e.g., the pericardium, aorta and other associated blood vessels), including ischemia-reperfusion injury; congestive heart failure; cardiac arrest; myocardial infarction; atherosclerosis, mitral valve leakage, atrial flutter, cardiotoxicity caused by compounds such as drugs (e.g., doxorubicin, herceptin, thioridazine and cisapride); cardiac damage due to parasitic infection (bacteria, fungi, rickettsiae, and viruses, e.g., syphilis, chronic *Trypanosoma cruzi* infection); fulminant cardiac amyloidosis; heart surgery; cardiac contractility/relaxation, heart transplantation; angioplasty, laparoscopic surgery, traumatic cardiac injury (e.g., penetrating or blunt cardiac injury, and aortic valve rupture), surgical repair of a thoracic aortic aneurysm; a suprarenal aortic aneurysm; cardiogenic shock due to myocardial infarction or cardiac failure; neurogenic shock and anaphylaxis. The tissue protective peptides and peptide analogs provided herein may also be used to treat those individuals at risk for heart disease such as cardiac failure (i.e., where the heart is not able to pump blood at a rate required by the metabolizing tissues, or when the heart can do so only with an elevated filling pressure). Such at risk patients would include patients having or being at risk of having cardiac infarction, coronary artery disease, myocarditis, chemotherapy, cardiomyopathy, hypertension, valvular heart diseases (most often mitral insufficiency and aortic stenosis) and toxin-induced cardiomyopathy (e.g. ethanol, cocaine, etc.) and the like.

The tissue protective peptides and peptide analogs provided herein may be used to treat or prevent conditions of, and damage to, the eyes, e.g., retinal tissue. Such disorders include, but are not limited to retinal ischemia, macular degeneration, retinal detachment, retinitis pigmentosa, arteriosclerotic retinopathy, hypertensive retinopathy, retinal artery blockage, retinal vein blockage, retinal edema, hypotension, and diabetic retinopathy.

In another embodiment, the tissue protective peptides and peptide analogs provided herein and principles described herein may be used to prevent or treat injury resulting from exposure to toxic agents, i.e. radiation or chemical damage to responsive tissue. In one embodiment, the above-noted peptides are useful as therapeutics for modulating the mediators of the body's response to toxic agents, or to suppress or inhibit the activity of such modulators. Additionally, the above-noted peptides are useful as therapeutics for the treatment, prevention, amelioration or management of damage, effects or symptoms of exposure to a toxic agent. The peptides may be used to treat exposure to various toxic agents, including biological, chemical or radiation agents.

These peptides may be used to treat the damages, effects, or symptoms due to biological agents such as of prions, viruses, microorganisms (bacteria and fungi), and some unicellular and multicellular eukaryotes (i.e., parasites), including, but not limited to, those biological toxins listed above in Section 4.2 (viii). Further the peptides provided herein may be used to prevent, treat, ameliorate, or manage the damage, effects or symptoms due to chemical agents. Such agents include, but are not limited to, blood agents, blister agents, nerve agents, pulmonary agents, and incapacitating agents. Additionally, the peptides provided herein may be used to prevent, treat, ameliorate or manage damage, effects or symptoms due to toxic exposure to industrial chemicals including but not limited to those listed in Section 4.2 (x). Damage, effects or symptoms due to exposure to a radiation agent are preventable, treatable, or manageable using the peptides provided herein. The peptides can prevent, treat, ameliorate, or manage the damage, effects or symptoms due to radioactive agents that include alpha, beta or gamma radiation, and more particularly may include, but are not limited to, $^{137}Cs$, $^{60}Co$, $^{241}Am$, $^{252}Cf$, $^{192}Ir$, $^{238}Pu$, $^{90}Sr$, $^{226}Ra$, $^{91}Sr$, $^{92}Sr$, $^{95}Sr$, $^{99}Mo$, $^{106}Ru$, $^{131}Sb$, $^{132}Te$, $^{139}Te$, $^{140}Ba$, $^{141}La$, $^{144}Ce$, $^{233}U$, $^{235}U$, $^{238}U$, $^{228}P$, $^{229}P$, $^{230}P$, $^{231}P$, $^{232}P$, $^{233}P$, $^{234}P$, $^{235}P$, $^{236}P$, $^{237}P$, $^{238}P$, $^{239}P$, $^{240}P$, $^{241}P$, $^{242}P$, $^{243}P$, $^{244}P$, $^{245}P$, $^{246}P$, $^{247}P$, and $^{131}I$. Further, one of ordinary skill in the art will recognize that the peptides may also be used to prevent, mediate, treat or ameliorate the damages, effects or symptoms due to the cumulative or synergistic use of these toxic agents (i.e., the use of a radioactive agent prior to dispersing a biological agent so that the victim's will be more susceptible to the biological agent, administering a vesicant agent in conjunction with a nerve agent to prevent the victims from effectively seeking refuge or aid, tainting bullets or shrapnel with biological or radioactive agents to inhibit or complicate the healing process, etc.) In one embodiment, peptides provided herein will be able to treat, mediate, ameliorate or prevent toxic effects on several different types of cells, organs, or tissues for example in two or more of the following central nervous, peripheral nervous, ophthalmic, cardiovascular, cardiopulmonary, respiratory, kidney, urinary, reproductive, musculoskeletal, skin, connective tissue, gastrointestinal, hematopoietic, endocrine, and metabolic. Further, a peptide provided herein would be effective as a therapeutic or preventive for more than one toxic agent within the same class (i.e., against more than one type of chemical, biological or radioactive agent—a preventive against a vesicant and nerve agents for example) or different classes of toxic agents (i.e. a therapeutic for exposure to a radioactive agent and a chemical agent). A further utility of the tissue protective peptides and peptide analogs provided herein is in the treatment of poisoning, such as neurotoxin poisoning (e.g., domoic acid shellfish poisoning), toxins (ethanol, cocaine, etc.), as the result of chemotherapeutic agents of radiation exposure (e.g., cisplatinum neurotoxicity); neurolathyrism; Guam disease; amyotrophic lateral sclerosis; and Parkinson's disease.

As mentioned above, provided herein are tissue protective peptides and peptide analogs for use in enhancing tissue function in responsive cells, tissues and organs in a mammal by peripheral administration of a tissue protective peptide as described above. Various diseases and conditions are amenable to treatment using this method. For example this method is useful for enhancing function in excitable tissues resulting in an increase in cognitive function even in the absence of any condition or disease. Further, the tissue protective cytokines are useful for improving the quality of wound healing (e.g. wound healing in critical ischemia and wound healing in punch biopsy healing), reducing the time required to heal, improving the quality of the healed tissues and reducing the incidence of adhesions resulting from the wound. See PCT/US2004/031789 filed Sep. 29, 2004 and published as WO 2005/032467. Further the tissue protective peptides provided herein may be useful in treating, preventing or managing the lesions on the skin or along the respiratory pathways induced by chemical agents such as blistering or vesicant agents or industrial chemicals.

These uses of the peptides provided herein are describe in further detail below and include enhancement of learning and training in both human and non-human mammals.

In another embodiment, the tissue protective peptides and peptide analogs provided herein may be useful generally for the prevention, therapeutic treatment, prophylactic treatment or management of various cancers or neoplastic disorders of the central nervous system, peripheral nervous system, gastrointestinal/digestive system, genitourinary system, adrenal, gynecological, head and neck, hematological/blood, musculoskeletal/soft tissue, respiratory, and breast. Examples of use include, but are not limited to, protection against and repair of injury resulting from cancers or neoplastic disorders listed in section 4.2(ix) and (xxiv). Further the peptides provided herein may be used for the prevention, therapeutic treatment, prophylactic treatment or management of various syndromes associated with neoplasms or cancers, including, but not limited to those listed above in Section 4.2 (xxvii). The peptides may be used in accordance with the method provided herein to address the above-noted syndromes. For example, the peptides may be administered to address hereditary syndromes such as Li Fraumeni, hereditary nonpolyposis colorectal cancer, familial adenomatous polyposis, and Von Hippel-Lindau syndrome by either delaying the onset of the neoplastic aspects of the disease, reducing the number of neoplastic growths associated with the syndrome, or in general enhancing the quality of life or the longevity of those patients afflicted with these conditions. The peptides may also be administered prophylactically to address syndromes related to certain treatment, chemotherapy or radiation therapy, of the neoplastic disorder or cancer, such as androgen deprivation syndrome, therapy related myelodysplastic syndrome or somnolence syndrome, in the hopes of preventing the syndromes or reducing the severity of the syndrome.

Further, the peptides may be used to treat or prevent cachexia and diseases related to cachexia. Such diseases include, but are not limited to cancer cachexia, anorexia, asthenia, anemia, tuberculosis, AIDS, congestive heart failure, renal failure, liver failure, chronic obstructive pulmonary disease, emphysema, inhalation emphysema, muscle atrophy, diabetes, and endotoxinemia.

Conditions and diseases treatable or preventable using tissue protective peptides and peptide analogs provided herein include but are not limited to mood disorders, anxiety disorders, depression, autism, attention deficit hyperactivity disorder, and cognitive dysfunction. These conditions benefit from enhancement of neuronal function. Other disorders treatable in accordance with the teachings provided herein include sleep disruption, for example, sleep apnea and travel-related disorders, subarachnoid and aneurismal bleeds, hypotensive shock, concussive injury, traumatic brain injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable or preventable using tissue protective peptides and peptide analogs provided herein include mitochondrial dysfunction, of either a hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. A tissue protective peptide or peptide analog optimizes failing function in a variety of mitochondrial diseases. As mentioned above, hypoxic conditions adversely affect excitable tissues. The excitable tissues include, but are not limited to, neuronal tissues such as tissue of the peripheral nervous system (ear and retina) and central nervous system (brain and spinal cord); cardiovascular tissue such as the cells of the heart and associated nerves; and glandular tissue such as the pancreas where T-type calcium channels along with cell-to-cell gap junctions participate in secretion of insulin. An exemplary list of excitable tissues includes, but is not limited to, organs and tissues that include nerves, skeletal muscle, smooth muscle, cardiac muscle, uterus, central nervous system, spinal cord, brain, retina, olfactory system, and auditory system. In addition to the conditions described above, the tissue protective peptides and peptide analogs provided herein are useful in the treatment of inhalation poisoning such as carbon monoxide and smoke inhalation, severe asthma, adult respiratory distress syndrome, and choking and near drowning. Further conditions which create hypoxic conditions or by other means induce responsive tissue, such as excitable tissue damage include hypoglycemia that may occur in inappropriate dosing of insulin, or with insulin-producing neoplasms (insulinoma).

Various neuropsychologic disorders which are described to originate from excitable tissue damage are treatable using tissue protective peptides and peptide analogs provided herein. Chronic disorders in which neuronal damage is involved and for which treatment or preventable by the present peptides and peptide analogs include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's disease, cerebral and progressive supranuclear palsy, Guam disease, Lewy body dementia, prion diseases, such as spongiform encephalopathies, e.g., Creutzfeldt-Jakob disease, Huntington's disease, neuritic dystrophy, neuropathy, neuropathy (cis-platinum-induced), neuropathy (diabetes induced), neuropathy (autonomic; diabetes induced), neuropathy (inflammatory), neuropathy (peripheral), pain, post-status epilepticus, myotonic dystrophy, Friedreich's ataxia and other ataxias, as well as Gilles de La Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical Manual of Mental Disorders (DSM).

A further group of conditions treatable or preventable using tissue protective peptides and peptide analogs provided herein include kidney diseases such as renal artery occlusion, renal injury, acute renal injury, renal artery occlusion and reperfusion, renal failure, acute and chronic, chronic kidney disease, renal ischemia, kidney ischemia-reperfusion, bilateral renal ischemia, and nephropathy (e.g., kidney damage, diabetic nephropathy, contrast or hypertensive nephropathy). Blood supply to the kidneys can be cut off due to several causes including shock from infections invading the bloodstream (septicemia), internal or external hemorrhaging, hemorrhagic shock, multiple organ failure, loss of fluid from the body as a result of severe diarrhea or burns, reactions to transfusions, cardiac arrest or arrhythmias, surgical trauma and kidney transplantations. The reduced flow of blood to the kidneys resulting from the above conditions may reduced blood flow to dangerously low levels for a time period great enough to cause the development of acute renal injury or acute renal failure. The depressed blood flow also results in necrosis, or tissue death, in the kidney, damaging the renal tubular cells. Renal failure may also result from diseases (interstitial and diabetic) nephrotic syndromes, infections, injury (CPB-induced), toxins (contrast-induced, chemotherapy-induced, cyclosporine), autoimmune inflammation (e.g. Lupus, erythrocytosis, etc.) The tissue protective peptides and peptide analogs provided herein assist in the repair or prevention of this damage helping to ameliorate acute renal failure. Further, the peptides provided herein may be used to treat, prevent or ameliorate diseases or disorders of the urinary tract including, but not limited, urinary tract infections, irritable bladder, bacterial invasion of bladder epithelial cells, and trauma or radiation injury to the bladder.

Table 1 lists additional exemplary, non-limiting indications as to the various conditions and diseases amenable to treatment by the aforementioned tissue protective peptides and peptide analogs.

TABLE 1

DISEASES AND DISORDERS AMENABLE TO TREATMENT BY TISSUE PROTECTIVE PEPTIDES AND PEPTIDE ANALOGS

| Cell, tissue, or organ | Dysfunction or pathology | Condition or disease | Type |
|---|---|---|---|
| Heart | Ischemia | Coronary artery disease | Acute, chronic Stable, unstable |
| | | Myocardial infarction Angina | Dressler's syndrome |
| | | Congenital heart disease | Valvular Cardiomyopathy |
| | | Prinzmetal angina | |
| | | Cardiac rupture | Aneurysmatic |
| | | Angiitis | |
| | Arrhythmia | Tachy-, bradyarrhythmia | Stable, unstable Hypersensitive carotid sinus node |
| | | Supraventricular, ventricular Conduction abnormalities | |
| | Congestive heart failure | Left, right, bi-ventricular, systolic, diastolic | Cardiomyopathies, such as idiopathic familial, infective, metabolic, storage disease, deficiencies, connective tissue disorder, infiltration and granulomas, neurovascular |
| | | Myocarditis and pericarditis | Autoimmune, infective, idiopathic |
| | | Cor pulmonale | |
| | Radiation injury | | |
| | Blunt and penetrating trauma | Intrathoracal adhesions to surgery, infections, or inflammation | |
| | Toxins | Cocaine toxicity, adriamycin, heavy metals (cobalt) | |
| Vascular | Hypertension | Primary, secondary | |
| | Decompression sickness | | |
| | Fibromuscular hyperplasia | | |
| | Aneurysm | Dissecting, ruptured, enlarging | |
| | Cancer | Hemangioma hemangiopericytoma | Hemangiosarcoma, angiosarcoma |
| Lungs | Obstructive | Asthma | |
| | | Chronic bronchitis, Emphysema and airway obstruction | |
| | Ischemic lung disease | Pulmonary embolism, Pulmonary thrombosis, Fat embolism | |
| | Environmental lung diseases | | |
| | Interstitial lung disease | Pulmonary fibrosis, Idiopathic pulmonary fibrosis | |
| | Congenital | Cystic fibrosis | |
| | Cor pulmonale | | |
| | Trauma | | |

TABLE 1-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| | Pneumonia and pneumonitides | Infectious (including Avian Flu), parasitic, toxic, traumatic, burn, aspiration | |
| | Sarcoidosis | | |
| | Cancers and precancers | | Bronchial carcinooid, oat cell carcinoma |
| | Radiation injury | | |
| Pancreas | Endocrine | Diabetes mellitus, type I and II | Beta cell failure, dysfunction Diabetic neuropathy |
| | | Other endocrine cell failure of the pancreas | |
| | Exocrine | Exocrine pancreas failure | Pancreatitis |
| | Cancer and precancers | Islet cell adenoma, Insulinoma, gastrinoma | Islet Cell Carcinoma |
| Bone | Osteopenia | Primary Secondary | Hypogonadism Immobilization Postmenopausal Age-related Hyperparathyroidism Hyperthyroidism Calcium, magnesium, phosphorus, and/or vitamin D deficiency |
| | Osteomyelitis | | |
| | Avascular necrosis | | |
| | Trauma | | |
| | Paget's disease | | |
| | Cancer | Osteoma | Osteosarcoma |
| Skin | Alopecia | Areata Totalis | Primary Secondary Male pattern baldness |
| | Vitiligo | Localized Generalized | Primary Secondary |
| | Ulceration | Diabetic Decubitus Ischemia | Pressure sores, pressure ulcers, bed sores |
| | Peripheral vascular disease | Infection, self amputation | |
| | Surgical wounds, lacerations | | |
| | Burn injuries | | |
| | Radiation injuries | Cutaneous radiation syndrome | |
| | Cancers and precancers | Nevus, papilloma, seborrheic keratosis, skin adnexal tumors | Melanoma, squamous cell carcinoma, epidermoid carcinoma, basal cell carcinoma and malignant skin adnexal tumors |
| Autoimmune disorders | Lupus erythematosus, Sjogren's syndrome, Rheumatoid arthritis, Glomerulonephritis, Angiitis, Fibromyalgia, Ankylosing spondylitis | | |
| | Langerhans' histiocytosis | | |
| Eye | Optic neuritis | | |
| | Blunt and penetrating injuries, surgical wounds, infections, Sarcoid, Sickle C disease, Retinal detachment, Temporal arteritis | | |
| | Retinal ischemia, Macular degeneration, Retinitis pigmentosa, Arteriosclerotic retinopathy, Hypertensive retinopathy, Retinal | | |

TABLE 1-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| | artery blockage, Retinal vein blockage, Hypotension, Diabetic retinopathy, glaucoma and Macular edema | | |
| Embryonic and fetal disorders | Asphyxia Ischemia | | |
| | Cancers and precancers | Myxoma, hydatidiform mole | Myxosarcoma, chordoma, choriocarcinoma |
| CNS | Chronic fatigue syndrome, acute and chronic hypo-osmolar and hyperosmolar syndromes, AIDS Dementia, Electrocution Cerebral malaria | | |
| | Encephalitis | Rabies, Herpes | |
| | Meningitis | | |
| | Subdural hematoma | | |
| | Nicotine addiction | | |
| | Drug abuse and withdrawal | Cocaine, heroin, crack, marijuana, LSD, PCP, poly-drug abuse, ecstasy, opioids, sedative hypnotics, amphetamines, caffeine, alcohol | |
| | Obsessive-compulsive disorders | | |
| | Psychotic and depressive disorders | | |
| | Attention deficit and hyperactivity disorders | | |
| | Spinal stenosis, Transverse myelitis, Guillain Barré, Traumatic injury to peripheral nerves, spinal cord, or brain, Nerve root compression, Compression by tumor or vascular malformations, Heat stroke | Brain Trauma/Injury, Brain Trauma/Injury (blunt force), Brain Trauma/Injury (with hypotension-resuscitation). | |
| | Cancers and precancers | Ganglioneuroma, meningioma, schwannoma, neurilemmoma | Glioma (grades I-III), anaplastic, glioblastoma multiforme (Grade IV), neuroblastoma, medulloblastoma, malignant meningioma, malignant schwannoma |
| ENT | Tinnitus | | |
| | Meunière's syndrome | | |
| | Hearing loss | | |
| | Traumatic injury, barotraumas | | |
| Kidney | Renal failure | Acute, chronic | Vascular/ischemic, interstitial disease, diabetic kidney disease, nephritic syndromes, infections, injury, contrast-induced, chemotherapy-induced, cyclosporine, radiation-induced Cardio Pulmonary Bypass-induced |

TABLE 1-continued

DISEASES AND DISORDERS AMENABLE TO TREATMENT BY TISSUE PROTECTIVE PEPTIDES AND PEPTIDE ANALOGS

| Cell, tissue, or organ | Dysfunction or pathology | Condition or disease | Type |
|---|---|---|---|
| | Radiation injury | | |
| | Henoch Schönlein purpura | | |
| | Cancers or precancers | Renal Tubular adenoma | Renal Cell Carcinoma, hypernephroma |
| Striated muscle | Autoimmune disorders | Myasthenia gravis Dermatomyositis Polymyositis | |
| | Myopathies | Inherited metabolic, endocrine and toxic | |
| | Heat stroke | | |
| | Crush injury | | |
| | Rhabdomyolysis | | |
| | Mitochondrial disease | | |
| | Infection | Necrotizing fasciitis | |
| | Cancers or precancers | Rhabdomyoma | Rhabdomyosarcoma |
| Sexual dysfunction | Central and peripheral (e.g. erectile dysfunction) | Impotence secondary to medication, (diabetes) | |
| Liver | Hepatitis | Viral, bacterial, parasitic | |
| | Ischemic disease | | |
| | Cirrhosis, fatty liver | | |
| | Infiltrative/metabolic diseases, metabolic syndrome | Metabolic Syndrome (fat-induced), diet-induced insulin resistance, | |
| | Cancers or precancers | Hepatic adenoma | Hepatoma: Hepatocellular carcinoma |
| Gastrointestinal | Ischemic bowel disease | | |
| | Inflammatory bowel disease | | |
| | Necrotizing enterocolitis | | |
| | Wound healing post surgical or perforation | abdominal adhesions due to surgery or infections | |
| | Cancers or precancers | Carcinoid | Malignant Carcinoid |
| Organ transplantation | Treatment of donor, organ and recipient | Transplant rejection, graft rejection, delayed graft function, graft v. host disease, pancreatic islet cell transplantation | |
| | Growth of cell or tissue cultures for tissue regeneration, graft or transplantation | pancreatic islet cell transplantation or harvesting | |
| Reproductive tract | Infertility | Vascular Autoimmune Uterine abnormalities Implantation disorders | |
| | Cancers or precancers | | Seminoma, dysgerminoma, choriocarcinoma, embryonal carcinoma, endodermal sinus tumor, teratocarcinoma, Seroli-Leydig tumors, arrhenoblastoma, granulosetheca cell tumors, hilar cell tumors, lipid cell tumors |

TABLE 1-continued

DISEASES AND DISORDERS AMENABLE TO TREATMENT BY
TISSUE PROTECTIVE PEPTIDES AND PEPTIDE ANALOGS

| Cell, tissue, or organ | Dysfunction or pathology | Condition or disease | Type |
|---|---|---|---|
| Endocrine | Glandular hyper- and hypofunction | | |
| | Cancers or precancers | Basophilic adenoma, Eosinophilic adenoma, Chromophobe adenoma, Parathyroid adenoma, C cell hyperplasia, Pheochromocytoma | Parathyroid carcinoma, Medullary carcinoma of thyroid, Malignant Pheochromocytoma |
| General | Shock | Septic, hemodynamic | |
| | Cachexia, Cancer Cachexia | Anorexia, Asthenia, Anemia | |
| | Parasitemia | Malaria, trypanosomiasis, Leshmaniasis | |

As mentioned above, these diseases, disorders or conditions are merely illustrative of the range of benefits provided by the tissue protective peptides and peptide analogs provided herein. Accordingly, this disclosure generally provides preventative, therapeutic, or prophylactic treatment of the consequences of mechanical trauma or of human diseases. Prevention or therapeutic or prophylactic treatment for diseases, disorders or conditions of the CNS and/or peripheral nervous system are contemplated. Prevention or therapeutic or prophylactic treatment for diseases, disorders or conditions which have a psychiatric component is provided. Prevention or therapeutic or prophylactic treatment for diseases, disorders or conditions including but not limited to those having an ophthalmic, cardiovascular, cardiopulmonary, respiratory, kidney, urinary, reproductive, gastrointestinal, endocrine, or metabolic component is provided. The peptides may be useful for the prevention, therapeutic treatment, prophylactic treatment or management of diseases or disorders associated with tissue damages as well as the damages, effects or symptoms thereof in one or more organs or tissues, in some embodiments at least two, including, but not limited to, the brain, spinal cord, connective tissue, skin, gastrointestinal tract, reproductive organs, liver, heart, lung, kidney, urinary tract, pancreas, eyes and prostate.

8.3 Prevention, Treatment, Amelioration, or Management of the Damage, Effects, or Symptoms of Diseases, Disorders or Conditions In a further embodiment, the method of treatment provided herein is useful for preventing, treating, ameliorating, or managing the damage, effects, or symptoms of the above noted diseases and disorders. In particular, the current method of treatment can be used to address symptoms including, but not limited to, cachexia, carcinogenesis, sterilization, cataract formation, radiodermatitis, beta burns, gamma burns, loss of cells (in particular bone marrow, digestive tract cells), damage to the hematopoietic, gastrointestinal, central nervous, cardiovascular, skin, skin cytokine levels, and/or reproductive systems, acute radiation syndrome (feeling of nausea, vomiting, general illness and fatigue, immune system depression, loss of hair, uncontrollable bleeding (mouth, under the skin, kidneys), reduction of circulating proinflammatory cytokines after partial body gamma radiation, massive diarrhea, delirium, coma and death), chronic radiation syndrome, cutaneous radiation syndrome (inflammation, erythema, dry or moist desquamation, hair loss, blistering, reddening, ulceration, damage to sebaceous and sweat glands, atrophy, fibrosis, decreased or increased skin pigmentation, and necrosis), headaches, dizziness, nausea, vomiting, mucosal irritation, dysponea, impaired consciousness, coma, convulsions, tachy- and brady-dysrhythmias, hypotension, cardiovascular collapse, chronic cardiovascular disease such as cardiomyopathy, progressive heart failure, peripheral arterial insufficiency, acyanosis, bradycardia, myosis, excessive salivation, diarrhea, involuntary micturition, muscle fasciculation, initial depolarizing flaccid paralysis, spike discharges and convulsions, intermediate syndrome, neurotoxic esterase inhibition, organophosphate-induced delayed neuropathy, erythema, edema, necrosis and vesicles, melanoderma, tracheobronchitis, bronchospasms, bronchial obstruction, hemorrhagic pulmonary edema, respiratory failure, bacterial pneumonia, eye erythema, lachrymation, discomfort of the eyes, severe pain in the eyes, blepharospasm, iritis, blindness, bone marrow suppression, lewisite shock, hepatic necrosis, renal failure secondary to hypoperfusion, burning sensations (eyes, nasopharynx, oropharynx), burn injury, profuse tearing, rhinorrhoea, coughing hoarseness, dyspnoea, odynophagia, conjunctivitis, corneal injury, naso-orophangyal injury/edema, respiratory distress due to inflammation of the glottic structures, secretions, and/or lyrangospasms, acute respiratory syndromes, disorientation, behavioral modifications, and reactive airway dysfunction syndrome.

As mentioned above, these diseases or disorders associated with tissue damage or damage, effects, or symptoms resulting therefrom are merely illustrative of the range of disorders that can be addressed by the peptides used in the method provided herein. Accordingly, this disclosure generally provides preventative, therapeutic, or prophylactic treatment of a disease or disorder associated with tissue damage or damage associated with an effect, or a symptom of the disease or disorder.

Diseases or disorders associated with tissue damage or damage associated with an effect, or a symptom of the disease or disorder can be treated or prevented by administration of an effective amount of a peptide provided herein. In certain embodiments, provided herein are methods of treating or preventing a disease or disorder described herein comprising the step of administering to a subject having the disease or disorder an amount of a peptide provided herein effective to treat or prevent the disease or disorder. In one embodiment, a composition comprising an effective amount of one or more peptides provided herein, or a pharmaceutically acceptable salt thereof, is administered.

8.4 Treatment in Conjunction with Other Therapeutics for a Cumulative or Synergistic Effect In certain embodiments, provided herein are methods for treating, mediating, ameliorating or preventing a disease or disorder associated with tissue damage or damage associated with an effect, or a symptom of the disease or disorder, comprising administering to a patient in need thereof an effective amount of a peptide and another suitable therapeutic agent, each being administered according to a regime suitable for the medicament. This may be done to achieve additive, synergistic or offsetting (to counteract side effects of the therapeutic) benefits of the effects of the peptide and therapeutic agents. This includes the concurrent, substantially simultaneous, or non-concurrent administration of the peptide and suitable therapeutic agent. The non-concurrent administration of the peptide and a suitable therapeutic agent includes sequential, alternating, and acute vs. chronic administration of the peptides and suitable therapeutic agents. Also, the peptide and the suitable therapeutic agent may be administered in the same or separate pharmaceutical compositions, and if administered separately they may be administered via the same route of administration or different routes. Suitable therapeutic methods and agents may include, but are not limited to, carbamates (pyridostigmine, physostigmine, aminostigmine, neostigmine, synostigmine, Epastigmine, Mobam, decarbofuran), anticholingerics (trihexyphenidyle, benactyzine, Biperidene, Scopolamine, aprophen, atropine, hyoscin, adiphenine, Caramiphen, pentmethonium, Mecamylamine, Trihexyphenidyle) PANPAL, aminophenols (eseroline), organophosphates (TEPP, Paraxon, Ethyl-4-nitrophenylphosphate), tacrine, 7-MEO-TA, huperzine A, Cholinesterases (BuChE, AChE, triesterase, paraoxonase), oximes/reactivators (HI-6, PAM, Obidoxime, Trimedoxime, Methoxime, Hlo-7, BI-6, K048, K033, pralidoxime chloride (2-PAM Cl), P2S, TMB4, 2-PAMI), Suramine, Benzodiazepines, tubocurine, Memantine, Procyclidine, Nimodipin, Clonidine, pralidoxime, diazepam, enkephalins, phenylmethylsulfonyl fluoride, natrium bicarbonate, vitamin E analogs ($\alpha$-tocopherol succinate, $\gamma$-tocotrienol), superoxide dismutase/catalase mimic (EUK189), selenium, benzyl styryl sulfone, truncated flagellin, statins, genistein, galantamine, hypothermia, 5-androstenediol, CpG-oligodeoxynucleotides, antimicrobials, stem cell transplants, pancreatic islet cell transplantation, amifostine, Tempol, isoflavones, benzylsulfone analogs, GM-CSF, G-CSF, potassium iodide, aluminum hydroxide, Prussian blue, chelating agents (diethylenetriaminepentaacetate (Ca-DTPA), zinc diethylenetriaminepentaacetate (Zn-DTPA)), keratinocyte growth factor, intestinal peptide hormones, beta glucan, octreotide, pentoxifylline, angiotensin converting enzyme inhibitors, angiotensin II receptor blockers, methemoglobin formers (amyl nitrite, sodium nitrite), sodium thiosulfate, cobalt compounds (hydroxycobalamin (Vitamin B12a), toxoids, antitoxins, vaccines, passive antibodies, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel; Radiation: $\gamma$-radiation; Alkylating agents; Nitrogen mustards: cyclophosphamide, Ifosfamide trofosfamide, Chlorambucil; Nitrosoureas: carmustine (BCNU), Lomustine (CCNU), Alkyl sulphonates busulfan, Treosulfan; Triazenes: Dacarbazine; Platinum containing compounds: Cisplatin carboplatin, Plant Alkaloids; *Vinca* alkaloids: vincristine, Vinblastine, Vindesine, Vinorelbine; Taxoids: paclitaxel, Docetaxol; DNA Topoisomerase Inhibitors Epipodophyllins: etoposide, Teniposide, Topotecan, 9-aminocamptothecin irinotecan (Campto®), crisnatol; Mytomycins: Mytomycin C, Mytomycin C; Antimetabolites, Anti-folates: DHFR inhibitors: methotrexate, Trimetrexate; IMP dehydrogenase Inhibitors: mycophenolic acid, Tiazofurin, Ribavirin EICAR; Ribonucleotide reductase Inhibitors: hydroxyurea; deferoxamine; Pyrimidine analogs: Uracil analogs, 5-Fluorouracil, Floxuridine, Doxifluridine, Ratitrexed; Cytosine analogs: cytarabine (ara C) Cytosine arabinoside fludarabine; Purine analogs: mercaptopurine, Thioguanine; Hormonal therapies; Receptor antagonists: Anti-estrogens, Tamoxifen, Raloxifene megestrol; LHRH agonists: goserelin, Leuprolide acetate; Anti-androgens: flutamide, bicalutamide; Retinoids/Deltoids Vitamin D3 analogs: EB 1089, CB 1093, KH 1060; Photodyamic therapies: vertoporfin (BPD-MA), Phthalocyanine photosensitizer, Pc4 Demethoxy-hypocrellin A (2BA-2-DMHA) Cytokines: Interferon-$\alpha$, Interferon-$\gamma$, Tumor necrosis factor; Isoprenylation inhibitors: Lovastatin; Dopaminergic neurotoxins: 1-methyl-4-phenylpyridinium ion; Cell cycle inhibitors: staurosporine; Actinomycins: Actinomycin D, Dactinomycin; Bleomycins: bleomycin A2, Bleomycin B2, Peplomycin; Anthracyclines: daunorubicin, Doxorubicin (adriamycin), Idarubicin, Epirubicin, Pirarubicin, Zorubicin, Mitoxantrone; MDR inhibitors: verapamil; Ca.sup.2+ ATPase inhibitors: thapsigargin; TNF-$\alpha$ inhibitors/thalidomide angiogenesis inhibitors 3-(3,4-dimethoxy-phenyl)-3-(1-oxo-1,3-dihydro-isoindol-2-yl)-propionamide (SelC-IDs™) ImiDs™, Revlimid™, Actimid™. In another aspect, a pharmaceutical composition provided herein may include a peptide in a formulation with at least one small molecule that exhibits tissue protective functionality. Suitable small molecules include, but are not limited to, steroids (e.g., lazaroids and glucocorticoids), antioxidants (e.g., coenzyme $Q_{10}$, alpha lipoic acid, and NADH), anticatabolic enzymes (e.g., glutathione peroxidase, superoxide dismutase, catalase, synthetic catalytic scavengers, as well as mimetics), indole derivatives (e.g., indoleamines, carbazoles, and carbolines), nitric acid neutralizing agents, adenosine/adenosine agonists, phytochemicals (flavanoids), herbal extracts (ginko *biloba* and turmeric), vitamins (vitamins A, E, and C), oxidase electron acceptor inhibitors (e.g., xanthine oxidase electron inhibitors), minerals (e.g., copper, zinc, and magnesium), non-steriodal anti-inflammatory drugs (e.g., aspirin, naproxen, and ibuprofen), and combinations thereof. Additionally agents including, but not limited to, anti-inflammatory agents (e.g., corticosteroids, prednisone and hydrocortisone), glucocorticoids, steroids, non-steriodal anti-inflammatory drugs (e.g., aspirin, ibuprofen, diclofenac, and COX-2 inhibitors), beta-agonists, anticholinergic agents and methyl xanthines), immunomodulatory agents (e.g., small organic molecules, T cell receptor modulators, cytokine receptor modulators, T-cell depleting agents, cytokine antagonists, monokine antagonists, lymphocyte inhibitors, or anti-cancer agents), gold injections, sulphasalazine, penicillamine, anti-angiogenic agents (e.g., angiostatin), TNF-$\alpha$ antagonists (e.g., anti-TNF$\alpha$ antibodies), and endostatin), dapsone, psoralens (e.g., methoxalen and trioxsalen), anti-malarial agents (e.g., hydroxychloroquine), anti-viral agents, anti-histamines and antibiotics (e.g., erythromycin and penicillin) may be used in conjunction with the current pharmaceutical compositions.

In other embodiments, the present methods for treating, mediating, ameliorating or preventing a disease or disorder associated with tissue damage or damage associated with an effect, or a symptom of the disease or disorder further comprise administration of the peptides in conjunction with methods of treatment such as chemotherapy, radiation therapy (x-ray radiation, high-energy megavoltage (radiation of greater that 1 MeV energy), electron beam, orthovoltage x-ray radiation, gamma-ray emitting radioisotopes (radioactive isotopes of radium, cobalt and other elements)), hyperbaric chambers, heart bypass machine, angioplasty, hypothermia, surgery, angioplasty, etc. to achieve additive, synergistic or offsetting (to counteract side effects of the therapeutic method) benefits of the effects of the peptide and therapeutic method. As an example, in a specific embodiment, peptide can be administered to a patient that has undergone surgery as treatment for the cancer concurrently with chemotherapy or radiation therapy. In another specific embodiment, a chemotherapeutic agent or radiation therapy is administered prior or subsequent to administration of a peptide, by at least an hour, five hours, 12 hours, a day, a week, a month, or several months (e.g., up to three months). Additionally, provided herein are methods of treatment of cancer or neoplastic disease with a peptide as an alternative to chemotherapy or radiation therapy where the chemotherapy or the radiation therapy has proven or may prove too toxic, e.g., results in unacceptable or unbearable side effects, for the patient being treated. Alternatively, provided herein are methods of treatment wherein the peptide is administered prior to, simultaneously with or following treatment with chemotherapy or radiation in an effort to prevent or ameliorate the toxic side effects of the treatment method. As demonstrated in Example 2, the peptides administered in accordance with the current method are able to ameliorate the side-effects of cis-platinum a known chemotherapeutic. Although, the above examples relate to the treatment of cancers, it is understood that the peptides may be administered in conjunction with other methods of treatment in the art for diseases or disorders associated with tissue damage and damage associated with an effect, or a symptom of the disease or disorder including inflammation, and exposure to toxic agents to achieve synergistic, additive or offsetting results.

8.5 Formulation and Administration of Peptides

In one embodiment, the method provided herein provides that a pharmaceutical composition comprising a peptide can be administered systemically to protect or treat the targeted cells, tissue or organ. Such administration may be parenterally, via inhalation, or transmucosally, e.g., orally, bucally, nasally, rectally, intravaginally, sublingually, ocularly, submucosally or transdermally. In some embodiments, administration is parenteral, e.g., via intravenous or intraperitoneal injection, and also including, but is not limited to, intraarterial, intramuscular, intradermal and subcutaneous administration.

For other routes of administration, such as by use of a perfusate, injection into an organ, or other local administration, a pharmaceutical composition will be provided which results in similar levels of a peptide as described above. A level of about 15 pM-30 nM can be used.

The pharmaceutical compositions provided herein may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution can be a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds provided herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the compound, which can be in purified form, together with a suitable amount of carrier so as to provide the form for proper administration to the patient. The formulation should suit the mode of administration.

Formulations for increasing transmucosal adsorption of peptides such as long acting peptides are also contemplated. Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream can be used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal and pulmonary administration may comprise solid carriers such as powders (e.g. having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. Alternatively, inhalation of compounds directly into the lungs may be accomplished by inhalation deeply or installation through a mouthpiece into the oropharynx. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In one embodiment, pharmaceutical compositions provided herein are administered into the nasal cavity directly or into the lungs via the nasal cavity or oropharynx.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of a peptide may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering a peptide to multiple sites in the severed part as soon as practicable, even before the arrival of medical personnel on site, or arrival of the afflicted individual with severed toe in tow at the emergency room.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations can contain 10% to 95% active ingredient.

A perfusate composition may be provided for use in situ perfusion. Such pharmaceutical compositions may comprise levels of peptides, or a form of peptides not suitable for acute or chronic, local or systemic administration to an individual, but will serve the functions intended herein in as an organ bath, organ perfusate, or in situ perfusate prior to removing or reducing the levels of the peptide contained therein before exposing or returning the treated organ or tissue to regular circulation.

Also provided herein is a pharmaceutical pack or kit comprising one or more containers filled with one or more of the ingredients of the pharmaceutical compositions provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, a peptide can be delivered in a controlled-release system. For example, the peptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574, each of which is incorporated by reference herein in its entirety). In another embodiment, the compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used (see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105, (each of which is incorporated by reference herein in its entirety).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, supra, 1984, which is incorporated by reference herein in its entirety). Other controlled release systems are discussed in the review by Langer (1990, Science 249:1527-1533, which is incorporated by reference herein in its entirety).

In another embodiment, peptide, as properly formulated, can be administered by nasal, bucal, oral, rectal, vaginal, ocular, transdermal, parenteral, inhalation or sublingual administration.

In a specific embodiment, it may be desirable to administer a peptide provided herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. A non-limiting example of such an embodiment would be a stent or other scaffolding coated with a peptide provided herein implanted in a portion of the vasculature, duct, etc.

Selection of an effective dose will be readily determinable by a skilled artisan based upon considering several factors, which will be known to one of ordinary skill in the art. Such factors include the particular form of peptide, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

In another aspect, a perfusate or perfusion solution is provided for perfusion and storage of organs for transplant, the perfusion solution includes an amount of a peptide or peptide analog effective to protect responsive cells and associated cells, tissues or organs. Transplant includes but is not limited to allotransplantation, where an organ (including cells, tissue or other bodily part) is harvested from one donor and transplanted into a different recipient, both being of the same species; autotransplantation, where the organ is taken from one part of a body and replaced at another, including bench surgical procedures, in which an organ may be removed, and while ex vivo, resected, repaired, or otherwise manipulated, such as for tumor removal, and then returned to the original location or xenotransplantation, where tissues or organs or transplanted between species. In one embodiment, the perfusion solution is the University of Wisconsin (UW) solution (U.S. Pat. No. 4,798,824, hereby incorporated by reference herein in its entirety) which contains 5% hydroxyethyl starch (having a molecular weight of from about 200,000 to about 300,000 and substantially free of ethylene glycol, ethylene chlorohydrin, sodium chloride and acetone); 25 mM $KH_2PO_4$; 3 mM glutathione; 5 mM adenosine; 10 mM glucose; 10 mM HEPES buffer; 5 mM magnesium gluconate; 1.5 mM $CaCl_2$; 105 mM sodium gluconate; 200,000 units penicillin; 40 units insulin; 16 mg dexamethasone; 12 mg Phenol Red; and has a pH of 7.4-7.5 and an osmolality of about 320 mOsm/1 supplemented with an appropriate amount of a peptide provided herein. This particular perfusate is merely illustrative of a number of such solutions that can be adapted for the present use by inclusion of an effective amount of a peptide. In a further embodiment, the perfusate solution contains from about 1 to about 500 ng/ml of a peptide, or from about 40 to about 320 ng/ml peptide. As mentioned above, any form of peptide can be used in this aspect.

While the contemplated recipient of a peptide for the purposes herein throughout is a human, the methods herein apply equally to other mammals, particularly domesticated animals, livestock, companion, and zoo animals. However, the disclosure is not so limiting and the benefits can be applied to any mammal.

In further aspects of the ex-vivo methods, any peptide, such as but not limited to the ones described above, may be employed.

In another aspect, methods and compositions for preventing, treating or managing a disease or disorder associated with tissue damage or damage associated with an effect, or a symptom of the disease or disorder in cells, tissues or organs which are not isolated from the vasculature by an endothelial cell barrier are provided by exposing the cells, tissue or organs directly to a pharmaceutical composition comprising a peptide, or administering or contacting a pharmaceutical composition containing a peptide to the vasculature of the tissue or organ.

Similar to other tissue protective compounds based on erythropoietin, it is possible that the peptides provided herein may be transported from the luminal surface to the basement membrane surface of endothelial cells of the capillaries of organs with endothelial cell tight junctions, including, for example, the brain, retina, and testis. Thus, the effects of a disease or disorder associated with tissue damage or damage associated with an effect, or a symptom of the disease or disorder on cells across the barrier may be treated. While not wishing to be bound by any particular theory, after transcytosis of the peptide may interact with a tissue-protective receptor on a cell, for example, neuronal, eye (e.g., retinal), adipose, connective, hair, tooth, mucosal, pancreatic, endocrine, aural, epithelial, skin, muscle, heart, lung, liver, kidney, small intestine, adrenal (e.g. adrenal cortex, adrenal medulla), capillary, endothelial, testes, ovary, stem or endometrial cell, and receptor binding can initiate a signal transduction cascade resulting in the activation of a gene expression program within the responsive cell or tissue, resulting in the protection of the cell or tissue, or organ, from damage, such as by exposure to a toxic agent, inflammation, hypoxia, etc. In another embodiment, the peptide can be cross-linked to a compound that can cross the barrier, to be transported across the barrier in accordance with the teaching of PCT Application No. PCT/US01/49479, U.S. patent application Ser. Nos. 10/188,905 and 10/185,841, incorporated herein by reference.

Thus, methods for protecting a tissue from disease or disorder associated with tissue damage or damage associated with an effect, or a symptom of the disease or disorder are described in detail herein below.

In the practice of one embodiment, a mammalian patient is undergoing systemic chemotherapy for cancer treatment, including radiation therapy, which commonly has adverse effects such as nerve, lung, heart, ovarian or testicular damage. Administration of a pharmaceutical composition comprising a tissue protective peptide or peptide analog as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment, various organs are planned to be harvested from a victim of an automobile accident for transplant into a number of recipients, some of which required transport for an extended distance and period of time. Prior to organ harvesting, the donor is infused with a pharmaceutical composition comprising tissue protective peptides and peptide analogs as described herein. Harvested organs for shipment are perfused with a perfusate containing tissue protective peptides or peptide analogs as described herein, and stored in a bath comprising tissue protective peptides or peptide analogs. Certain organs are continuously perfused with a pulsatile perfusion device, utilizing a perfusate containing tissue protective peptides and peptide analogs in accordance with the present disclosure. Minimal deterioration of organ function occurs during the transport and upon implant and reperfusion of the organs in situ.

In another embodiment, a participant in a hazardous activity that exposes the individual to toxic agents, one could take a dose of a pharmaceutical composition containing a peptide sufficient to either prevent (i.e. delaying the onset of, inhibiting, or stopping), protect against, or mitigate the effects of exposure to a toxic agent. In particular, this method of treatment may have application in various professions involving contact with toxic agents, such as miners, chemical manufacturers, military personnel (soldiers, paratroopers), emergency personnel (police, fire, EMS, and disaster relief personnel), construction workers, food processors, and employees at power reactors.

In another embodiment, a surgical procedure to repair a heart valve requires temporary cardioplegia and arterial occlusion. Prior to surgery, the patient is infused with a tissue protective peptide or peptide analog. Such treatment prevents hypoxic ischemic cellular damage, particularly after reperfusion. Additionally, the pharmaceutical compositions provided herein may be used prophylactically to prepare an individual for surgery in an effort to limit the trauma associated with the surgical procedure or aide in the recovery of the individual from the surgical procedure. Although the present method of treatment using pharmaceutical compositions containing tissue protective peptides and peptide analogs provide a prophylactic use for surgical procedures, it may be particularly useful in procedures that induce temporary ischemic events including, but not limited to, bypass procedures (coronary bypass), angioplasty procedures, amputations, and transplantations, as well as, those performed directly upon responsive cells, tissues, or organs such as brain and spinal cord surgery, and open heart procedures. Such procedures may involve the use of cardiopulmonary (heart lung) bypass.

In another embodiment, in any surgical procedure, such as in cardiopulmonary bypass surgery, a tissue protective peptide or peptide analog provided herein can be used. In one embodiment, administration of a pharmaceutical composition comprising tissue protective peptides and peptide analogs as described above is performed prior to, during, and/or following the bypass procedure, to protect the function of brain, heart, and other organs.

In the foregoing examples in which a peptide is used for ex-vivo applications, or for in vivo applications to treat a disease or disorder associated with tissue damage or damages, effects or symptoms resulting therefrom, provided herein is a pharmaceutical composition in dosage unit form adapted for prevention, treatment or management of the damages and effects of exposure to a toxic agent or symptoms thereof which comprises an amount within the range from about 0.01 pg to 30 mg, 0.5 pg to 25 mg, 1 pg to 20 mg, 500 pg to 10 mg, 1 ng to 10 mg, 500 ng to 10 mg, 1 µg to 10 mg, 500 µg to 10 mg, or 1 mg to 10 mg of a peptide, and a pharmaceutically acceptable carrier. In one embodiment, the amount of peptide is within the range from about 0.5 pg to 1 mg. In one embodiment, the formulation contains peptides that are non-erythropoietic.

Furthermore, this restorative aspect is directed to the use of any peptides herein for the preparation of a pharmaceutical composition for the restoration of cellular, tissue or organ dysfunction, wherein treatment is initiated after, and well after, the initial insult responsible for the dysfunction. Moreover, treatment using peptides provided herein can span the course of the disease or condition during the acute phase as well as a chronic phase.

A peptide provided herein may be administered systemically at a dosage between about 1 ng and about 300 µg/kg body weight, e.g. about 5-150 µg/kg-body weight or about 10-100 µg/kg-body weight, per administration. For example, administration may be repeated hourly, daily, as long as clinically necessary, or after an appropriate interval, e.g., every 1-12 hours, every 6 to 12 hours, every 2-6 days, every 2-4 days, every 1 to 12 weeks, or every 1 to 3 weeks. In one embodiment, the effective amount of peptide and a pharmaceutically acceptable carrier may be packaged in a single dose vial or other container. In another embodiment, the peptides, which are capable of exerting the activities described herein but not causing an increase in hemoglobin concentration or hematocrit, are used. Such peptides can be used in instances wherein the methods provided herein are intended to be provided chronically.

TABLE 2

SEQUENCES

| SEQ ID No. | Description | Sequence |
|---|---|---|
| 1 | Tissue protective peptide | GDKARYEREM |
| 2 | Tissue protective peptide | GDKARYEREA |
| 3 | Tissue protective peptide | GDKA |
| 4 | Amphipathic peptide: calcitonin-Peptide A | ALSILVLLQAGS |
| 5 | Amphipathic peptide: Peptide B-corticotropin releasing hormone | VALLPCPPCRA |
| 6 | Amphipathic peptide: Peptide C-beta endorphin | NAIIKNAYKKG |
| 7 | Amphipathic peptide: Peptide D-glucagon | GSWQRSLQDTE |
| 8 | Amphipathic peptide: Peptide E-secretin | GGSAARPAPP |
| 9 | Amphipathic peptide: Peptide F-vasointestinal peptide | NALAENDTPYY |
| 10 | Amphipathic peptide: Peptide G-neuropeptide Y | GALAEAYPSKP |

TABLE 2-continued

SEQUENCES

| SEQ ID No. | Description | Sequence |
|---|---|---|
| 11 | Amphipathic peptide: Peptide H-gonadotropin releasing hormone | GCSSQHWSYGL |
| 12 | Amphipathic peptide: Peptide I-parathyroid hormone | VMIVMLAICFL |
| 13 | Amphipathic peptide: Peptide J-pancreatic polypeptide | LRRYINMLTRP |
| 14 | Amphipathic peptide: Peptide K-calcitonin gene related peptide | LALSILVLYQA |
| 15 | Chimeric peptide of SEQ ID NO: 3 and 14 | GDKALRRYINMLTRP |
| 16 | Chimeric peptide of SEQ ID NO: 3 and 14 with TR replacement | GDKALRRYINMLTRTR |

9. EXAMPLES

The following examples are provided by way of illustration, and not by way of limitation.

Example 1: Efficacy in a Model of Neuropathic Pain

This example shows that a tissue protective peptide protects animals from nerve injury and pain.

The rats used in this study were eight-week-old female Sprague-Dawley rats (Charles River, Maastricht, The Netherlands). Animals were anesthetized with 6% sevoflurane induction and 3% maintenance. A small incision was made in the lateral surface of the left hind limb of the animal, exposing the muscles. The trifurcation of the sciatic nerve was revealed by blunt preparation between the two heads of the biceps femoris muscle. Next, the tibial and common peroneal nerves were tightly ligated with 5-0 silk in rats and 6-0 silk in mice and cut to remove 2-4 mm of the distal nerve. The sural nerve was left intact. In order to prevent spontaneous nerve reconnection, the transected nerves were displaced. During the surgical procedure, great care was taken not to stretch or touch the sciatic or sural nerves. The wound was closed in two layers with 4-0 silk in rats and 6-0 silk in mice and a single dose of 0.01 and 0.05 mg/kg buprenorphine was administered in rats and mice, respectively, to relieve postoperative pain. After exposure spared nerve injury (SNI) was induced and the wound was closed in two layers with 4-0 (rats) or 6-0 (mice) silk and a single dose of 0.01 (rats) mg/kg buprenorphine was administered to relief postoperative pain. During the surgical procedure, great care was taken not to stretch or touch the exposed nerves.

Treatment was initiated at 24-h after induction of the SNI: five 30 µg/kg peptide (GDKA (SEQ ID NO: 3), GDKARYEREM (SEQ ID NO: 1), or positive control) intraperitoneal injections at 2 day intervals. The peptide of SEQ ID NO: 282 from U.S. Pat. No. 8,853,358 was used as the positive control. Tactile allodynia was tested with the use of different von Frey hairs (Semmes-Weinstein Monofilaments, North Coast Medical Inc., San Jose, Calif.) with increasing stiffness (0.004-15 g) causing incremental forces to be exerted on the plantar surface of the affected hind paw. The hairs were applied 10 times at intervals of 1-2 s to slightly different loci within the test area. The force necessary to evoke a pain reflex by a brisk paw withdrawal was recorded and no further filaments were applied to the paw that showed a response.

As shown in FIG. 1, animals receiving vehicle show an increased sensitivity to touch. In contrast, animals receiving peptide provided herein did not show an increased sensitivity.

Example 2: Activation of Akt Phosphorylation

This example shows that a tissue protective peptide activates AKT.

HUVECs were purchased from Cell Applications (San Diego, Calif.) and grown in medium EGM-2 supplemented with 2% fetal calf serum (FCS) and penicillin/streptomycin (P/S) at 37° C. under air containing 5% $CO_2$ in a humidified incubator. Preliminary experiments showed that phosphorylation of Akt reached a maximum 10 minutes following stimulation by compounds that activated the tissue protective receptor. After HUVECs were treated with GDKA (SEQ ID NO: 3) peptide, cell lysates were prepared and Western blot was performed using anti-Akt and anti-phospho-Akt antibodies (Cell Signaling Technology, Danvers, Mass.). Briefly, cell lysates were subjected to SDS-PAGE, and transferred to nitrocellulose membranes (Amersham Biosciences, Piscataway, N.J.). The membrane was blocked for 1 h at room temperature with PBS containing 2% BSA and 0.05% Tween 20. The blots were incubated overnight at 4° C. or for 4 h at room temperature with a primary antibody against phospho-Akt, followed by incubation for 1 h with a secondary, horseradish peroxidase-conjugated antibody. Then the blots were reprobed with an antibody against Akt to confirm equal protein loading. Immuno-reactive bands were visualized using ECL (Amersham Biosciences, Piscataway, N.J.).

As shown in FIG. 2, GDKA (SEQ ID NO: 3) peptide activated AKT.

Example 3: Tissue Protective Activities of Gdka (Seq Id No: 3) Peptide

This example shows that that a tissue protective peptide protects animals from nerve damage and neuropathy.

As demonstrated by Beiswenger et al., an increase in thermal withdrawal latency correlates with the loss of epidermal innervation, which is shown as a reduction in the density of intra-epidermal nerve fibers, four weeks after the initiation of STZ-induced diabetis in mice (Beiswenger et al., 2008 Neurosci Lett. 442:267). Smith et al. also reported that loss of intra-epidermal nerve fibers is a valid surrogate measure of neuropathy severity and progression (Smith et al., 2006 Diabetes Care 29:1294). Thus, the effect of a peptide with amino acid sequence GDKA (SEQ ID NO:3) on thermal withdrawal latency in STZ-induced diabetic mice was tested to demonstrate its ability to protect from nerve damage in diabetic neuropathy.

Briefly, male Swiss Webster mice were given a single injection of STZ (180 mg/kg i.p.) to induce insulin-deficient diabetes. Hyperglycemia was confirmed 3 days later, and to ensure induction of sufficient neuropathy, only mice with blood glucose levels exceeding 15 mmol/l were used. After four weeks of untreated diabetes, tissue protective peptides or control treatment (phosphate buffered saline (PBS)) was administered as eye drops (50 microliters of 50 nanomolar solution to both eyes for five days/week. The peptide of SEQ ID NO: 282 from U.S. Pat. No. 8,853,358 was used as the positive control. After 12 weeks of therapy, mice were tested for paw thermal sensitivity. To measure thermal withdrawal latency, mice were placed in enclosures with a warmed glass floor and a mobile radiant heat source was directed at the plantar surface of one hind paw. The heat was increased 0.9° C. per second to ensure the paw withdrawal response involved activation of heat-sensitive C-fibers (Yeomans et al., 1996 Pain 68:133). The time from initiation of heating to paw withdrawal was recorded in 4 separate trials 5 minutes apart, with the median value of the last 3 trials used for each mouse.

As shown in FIG. 3, diabetic mice receiving PBS treatment exhibited an increased thermal latency (thermal threshold), which is consistent with the development of neuropathy. In contrast, mice receiving GDKA (SEQ ID NO: 3) peptide exhibited a normal thermal threshold that was comparable to that of non-diabetic mice or diabetic mice treated with the positive control. The thermal threshold of mice receiving GDKA (SEQ ID NO: 3) peptide was also significantly lower than the PBS-treated diabetic mice. These results demonstrate that GDKA (SEQ ID NO: 3) peptide protects animals from nerve damage and neuropathy.

This disclosure is not to be limited in scope by the specific embodiments described which are intended as single illustrations of individual aspects of the disclosure, and functionally equivalent methods and components are within the scope of the disclosure. Indeed various modifications of the disclosure, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. An isolated peptide comprising the amino acid sequence consisting of GDKARYEREA (SEQ ID NO:2).

2. A pharmaceutical composition comprising the isolated peptide of claim 1 and a pharmaceutically acceptable carrier.

3. The pharmaceutical composition of claim 2, wherein the composition is formulated for oral, intranasal, ocular, inhalational, transdermal, rectal, sublingual, or parenteral administration.

4. The pharmaceutical composition of claim 2, wherein the composition is formulated as a perfusate solution.

5. A method of producing the isolated peptide of claim 1, comprising the step of chemically synthesizing the peptide.

* * * * *